US009782144B2

(12) United States Patent
Kuwabara

(10) Patent No.: US 9,782,144 B2
(45) Date of Patent: Oct. 10, 2017

(54) RADIOGRAPHIC IMAGING SYSTEM, RADIOGRAPHIC IMAGING DEVICE, RADIOGRAPHIC IMAGING DEVICE CONTROL METHOD, AND PROGRAM STORAGE MEDIUM

(71) Applicant: FUJIFILM CORPORATION, Minato-ku, Tokyo (JP)

(72) Inventor: Takeshi Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 260 days.

(21) Appl. No.: 14/631,844

(22) Filed: Feb. 26, 2015

(65) Prior Publication Data

US 2015/0245808 A1    Sep. 3, 2015

(30) Foreign Application Priority Data

Mar. 3, 2014 (JP) .................................. 2014-041013
Dec. 19, 2014 (JP) .................................. 2014-257920

(51) Int. Cl.
*A61B 6/00*   (2006.01)

(52) U.S. Cl.
CPC .............. *A61B 6/54* (2013.01); *A61B 6/4208* (2013.01); *A61B 6/4233* (2013.01);
(Continued)

(58) Field of Classification Search
CPC ... A61B 6/4208; A61B 6/4233; A61B 6/4266; A61B 6/4283; A61B 6/5258; A61B 6/54; A61B 6/542; A61B 6/56; A61B 6/566
(Continued)

(56) References Cited

U.S. PATENT DOCUMENTS 6,307,915 B1 * 10/2001 Fröjdh ...................... G01T 1/17
                                                                    348/E3.02
7,006,598 B2 *  2/2006 Morii ................. H01L 27/14658
                                                                    250/370.07
(Continued)

FOREIGN PATENT DOCUMENTS

JP    2011-72775 A    4/2011
JP    2011-072775 A   4/2011
(Continued)

OTHER PUBLICATIONS

Asahi Glass Co., Ltd., "AGC Develops World's Thinnest Sheet Float Glass at Just 0.1 MM", press release, Tokyo, May 16, 2011. (www.agc.com/english/news/2011/0516e.pdf).
(Continued)

*Primary Examiner* — Allen C. Ho
(74) *Attorney, Agent, or Firm* — SOLARIS Intellectual Property Group, PLLC

(57) ABSTRACT

A radiographic imaging system includes plural radiographic imaging devices that image a same subject. The radiographic imaging device includes: a radiation detector; a detection unit that detects whether or not application of the radiation has been started based on electrical signals indicating detection results of sensors that detect the application of the radiation and that are disposed in correspondence to the radiation detector; a determination unit that determines whether or not noise is superimposed on the electrical signals after the detection unit has detected whether or not the application of the radiation has been started; and a communication unit that is connected to another radiographic imaging device and transmits to and receives from the other connected radiographic imaging device a detection result signal indicating the detection result of the detection
(Continued)

unit and a determination result signal indicating the determination result of the determination unit.

13 Claims, 26 Drawing Sheets

(52) U.S. Cl.
CPC .......... *A61B 6/4266* (2013.01); *A61B 6/5258* (2013.01); *A61B 6/542* (2013.01); *A61B 6/548* (2013.01); *A61B 6/56* (2013.01); *A61B 6/566* (2013.01)

(58) Field of Classification Search
USPC ................. 378/62, 98.8, 98.7; 250/370.09
See application file for complete search history.

(56) References Cited

U.S. PATENT DOCUMENTS

| | | | | |
|---|---|---|---|---|
| 7,078,701 B2* | 7/2006 | Ishii | ............... | G01T 1/2928 250/370.01 |
| 7,079,189 B2* | 7/2006 | Tsujii | ............... | G01T 1/2928 250/208.4 |
| 7,382,859 B2* | 6/2008 | Nokita | ............... | A61B 6/00 250/370.09 |
| 8,461,543 B2* | 6/2013 | Nishino | ............... | G01T 7/00 250/370.08 |
| 8,507,871 B2* | 8/2013 | Okada | ............... | H04N 5/32 250/370.08 |
| 8,513,611 B2* | 8/2013 | Okada | ............... | H04N 5/32 250/366 |
| 8,536,534 B2* | 9/2013 | Okada | ............... | H01L 27/14603 250/366 |
| 8,542,796 B2* | 9/2013 | Sato | ............... | A61B 6/5205 378/62 |
| 8,575,557 B2* | 11/2013 | Okada | ............... | H04N 5/32 250/370.08 |
| 8,637,828 B2* | 1/2014 | Okada | ............... | G01T 1/24 250/370.08 |
| 8,637,832 B2* | 1/2014 | Watanabe | ............... | G01T 1/247 250/394 |
| 8,669,531 B2* | 3/2014 | Okada | ............... | G01T 1/247 250/370.09 |
| 8,680,470 B2* | 3/2014 | Okada | ............... | H04N 5/32 250/370.08 |
| 8,742,354 B2* | 6/2014 | Shimizukawa | ............... | G01T 1/16 250/354.1 |
| 8,785,863 B2* | 7/2014 | Oda | ............... | G01T 1/17 250/366 |
| 8,829,455 B2* | 9/2014 | Nakatsugawa | ............... | A61B 6/4233 250/370.09 |
| 8,841,620 B2* | 9/2014 | Okada | ............... | H04N 5/32 250/366 |
| 8,841,628 B2* | 9/2014 | Kitano | ............... | H01L 27/14663 250/393 |
| 8,853,644 B2* | 10/2014 | Nakahashi | ............... | A61B 6/4283 250/394 |
| 8,879,686 B2* | 11/2014 | Okada | ............... | H04N 5/32 378/19 |
| 8,879,689 B2* | 11/2014 | Ohta | ............... | A61B 6/4233 378/108 |
| 8,903,048 B2* | 12/2014 | Kitano | ............... | A61B 6/4233 378/115 |
| 8,923,482 B2* | 12/2014 | Tajima | ............... | H05G 1/44 378/108 |
| 8,952,335 B2* | 2/2015 | Sato | ............... | G01T 1/247 250/214.1 |
| 8,971,494 B2* | 3/2015 | Tajima | ............... | A61B 6/542 378/108 |
| 8,983,035 B2* | 3/2015 | Noma | ............... | H05G 1/64 250/214 DC |
| 9,006,675 B2* | 4/2015 | Okada | ............... | G01T 1/243 250/394 |
| 9,020,097 B2* | 4/2015 | Iwakiri | ............... | A61B 6/4283 378/42 |
| 9,042,519 B2* | 5/2015 | Kuwabara | ............... | A61B 6/4283 378/114 |
| 9,050,051 B2* | 6/2015 | Nakatsugawa | ............... | A61B 6/4233 |
| 9,055,922 B2* | 6/2015 | Kuwabara | ............... | A61B 6/542 |
| 9,060,731 B2* | 6/2015 | Kuwabara | ............... | A61B 6/4233 |
| 9,060,738 B2* | 6/2015 | Kuwabara | ............... | A61B 6/542 |
| 9,063,239 B2* | 6/2015 | Oda | ............... | G01T 1/24 |
| 9,078,624 B2* | 7/2015 | Sugizaki | ............... | G01T 1/2928 |
| 9,091,770 B2* | 7/2015 | Okada | ............... | G01T 1/247 |
| 9,097,811 B2* | 8/2015 | Watanabe | ............... | G01T 1/243 |
| 9,101,328 B2* | 8/2015 | Tsuji | ............... | G01T 1/026 |
| 9,158,004 B2* | 10/2015 | Oda | ............... | G01T 1/17 |
| 9,194,964 B2* | 11/2015 | Ito | ............... | H04N 5/32 |
| 9,232,620 B2* | 1/2016 | Tajima | ............... | H05G 1/42 |
| 9,250,333 B2* | 2/2016 | Okada | ............... | G01T 1/17 |
| 9,250,335 B2* | 2/2016 | Okada | ............... | G01T 1/2928 |
| 9,258,464 B2* | 2/2016 | Ohta | ............... | A61B 6/487 |
| 9,259,201 B2* | 2/2016 | Sato | ............... | A61B 6/542 |
| 9,282,943 B2* | 3/2016 | Oda | ............... | H04N 5/32 |
| 9,301,725 B2* | 4/2016 | Kaneko | ............... | A61B 6/4233 |
| 9,322,928 B2* | 4/2016 | Iwakiri | ............... | A61B 6/4233 |
| 9,335,422 B2* | 5/2016 | Oda | ............... | G01T 1/17 |
| 9,351,699 B2* | 5/2016 | Kuwabara | ............... | A61B 6/542 |
| 9,360,562 B2* | 6/2016 | Sato | ............... | A61B 6/4233 |
| 9,366,766 B2* | 6/2016 | Okada | ............... | G01T 1/2018 |
| 9,462,990 B2* | 10/2016 | Kuwabara | ............... | A61B 6/54 |
| 9,513,379 B2* | 12/2016 | Nishino | ............... | G01T 1/2018 |
| 9,521,987 B2* | 12/2016 | Tajima | ............... | A61B 6/08 |
| 9,579,076 B2* | 2/2017 | Tajima | ............... | H05G 1/44 |
| 9,651,685 B2* | 5/2017 | Okada | ............... | H01L 27/14605 |
| 9,668,331 B2* | 5/2017 | Takahashi | ............... | H04N 5/32 |
| 2011/0057111 A1 | 3/2011 | Nishino | | |
| 2015/0043715 A1 | 2/2015 | Kuwabara | | |

FOREIGN PATENT DOCUMENTS

| | | |
|---|---|---|
| JP | 2012-85794 A | 5/2012 |
| JP | 2014-006235 A | 1/2014 |

OTHER PUBLICATIONS

English language translation of the following: Office action dated Dec. 6, 2016 from the JPO in a Japanese patent application No. 2014-257920 corresponding to the instant patent application. This office action translation is submitted now in order to supplement the understanding of the cited references which are being disclosed in the instant Information Disclosure Statement.

* cited by examiner

FIG.7
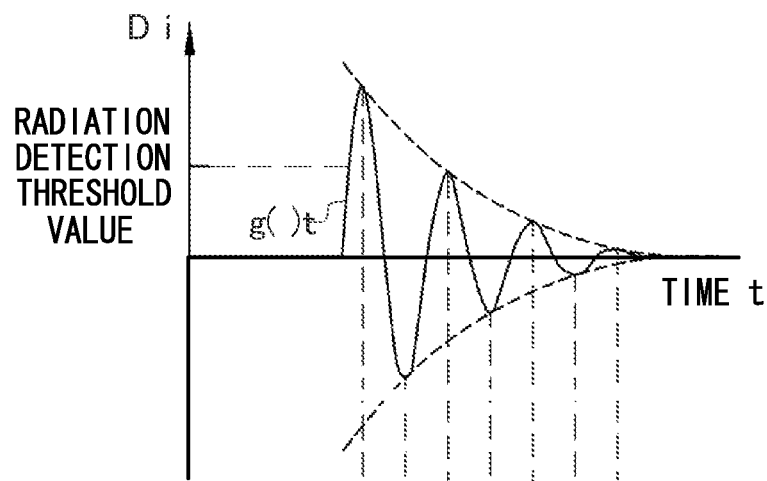
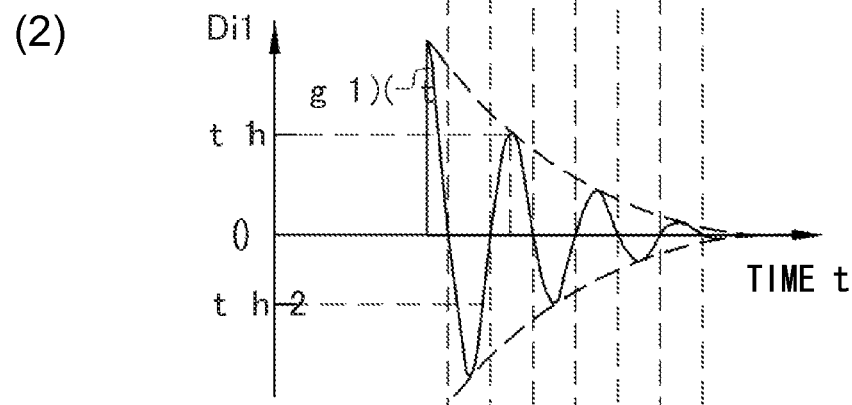
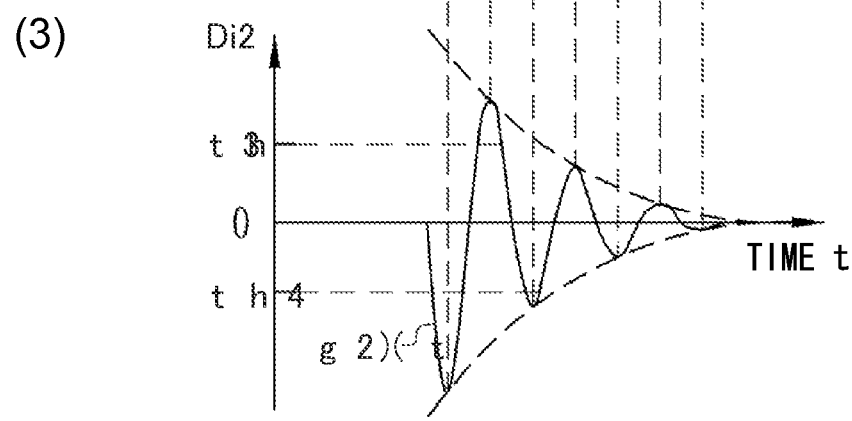

RADIOGRAPHIC IMAGING SYSTEM, RADIOGRAPHIC IMAGING DEVICE, RADIOGRAPHIC IMAGING DEVICE CONTROL METHOD, AND PROGRAM STORAGE MEDIUM

CROSS-REFERENCE TO RELATED APPLICATIONS

This application claims priority under 35 USC 119 from Japanese Patent Applications No. 2014-041013 filed on Mar. 3, 2014, and No. 2014-257920 filed on Dec. 19, 2014, the disclosures of which are incorporated by reference herein.

BACKGROUND OF THE INVENTION

Field of the Invention

The present invention relates to a radiographic imaging system, a radiographic imaging device, a radiographic imaging device control method, and a program storage medium.

Related Art

Conventionally, as radiographic imaging devices that image a subject, those that perform radiographic imaging for the purpose of medical diagnosis, for example, have been known. The radiographic imaging device detects radiation that has been applied from a radiation application device and passed through the subject to thereby capture a radiographic image. The radiographic imaging device performs radiographic imaging by collecting and reading out electric charges (charges) generated in accordance with the applied radiation.

Technologies that perform imaging using plural radiographic imaging devices for the purpose of imaging a large subject such as a long subject, for example, have been known.

For example, Japanese Patent Application Laid-open (JP-A) No. 2012-85794 describes a radiographic imaging system equipped with plural radiation detectors. JP-A No. 2011-72775 describes a radiographic imaging system in which the imaging plane is elongated by disposing plural electronic cassettes adjacent to one another.

A radiographic imaging device equipped with an application detection unit has been known, in which the application detection unit is equipped with sensor portions, which are configured by photoelectric conversion elements or the like that generate charges when radiation or light into which radiation has been converted is applied thereto, and switch elements, which read out the charges generated by the sensor portions. The application detection unit also detects that application of the radiation has been started (radiographic imaging has been started) based on the charges that have been read out from the switch elements.

In a case in which the radiographic imaging system is equipped with plural radiographic imaging devices, the entire imaging plane for imaging the subject becomes long, so there are cases in which the amount of radiation applied differs among the radiographic imaging devices. In such a case, there is a concern that even though the start of the application of the radiation has been detected in some of the radiographic imaging devices, the start of the application of the radiation is not detected in the other radiographic imaging devices.

For example, in a case of applying radiation near the center of an elongated imaging plane, the radiographic imaging device disposed near the center may detect the starts of the application of the radiation. However, the radiographic imaging devices arranged on the end sides may not detect the start of the application of the radiation, or that the timing when they detect the start of the application of the radiation may be later, because the amount of radiation applied thereto is smaller than the amount of radiation applied to the radiographic imaging device disposed near the center.

In such a case, the radiographic imaging device that has detected the start of the application of the radiation starts accumulating the charges. However, the radiographic imaging devices that have not yet detected the start of the application do not start accumulating the charges. For that reason, the imaging operations end up differing for each radiographic imaging device, and in terms of the radiographic imaging devices for imaging an elongated radiographic image overall, the imaging operations may no longer be uniform. In the technology described in JP-A No. 2012-85794, there is a concern that such a problem may arise in the case of detecting the start of the application of the radiation in each of the radiation detectors.

In the technology described in JP-A No. 2011-72775, since the start of the application of the radiation is not detected by the individual electronic cassettes, and control for accumulating the charges is performed by a separately disposed device, time is required until the charge accumulation operation is started.

SUMMARY

The present invention has been made in light of the above and provides a radiographic imaging system, a radiographic imaging device, a radiographic imaging device control method, and a program storage medium that may improve the trackability of incident radiation in a radiographic imaging system equipped with plural radiographic imaging devices that independently detect the start of application of radiation and perform imaging operations.

A first aspect of the present invention is a radiographic imaging system including plural radiographic imaging devices that image a same subject with same applied radiation, each of the plural radiographic imaging devices including: a radiation detector including plural pixels, each of the plural pixels including a sensor portion that generates a charge corresponding to an amount of applied radiation and accumulates the generated charge, and a switch element for reading out the charge from the sensor portion; a detection unit configured to detect whether or not application of the radiation has been started with respect to the radiation detector based on electrical signals indicating detection results of sensors that detect the application of the radiation and that are disposed in correspondence to the radiation detector; a determination unit configured to determine whether or not noise is superimposed on the electrical signals after the detection unit has detected whether or not the application of the radiation has been started with respect to the radiation detector; and a communication unit that is connected to another radiographic imaging device and transmits to and receives from the other connected radiographic imaging device a detection result signal indicating the detection result of the detection unit and a determination result signal indicating the determination result of the determination unit.

In the first aspect, the detection result signal and the determination result signal may be binary signals.

In the first aspect, each of the plural radiographic imaging devices may further include a control unit configured to effect control of starting accumulation of the charges generated by the sensor portions in a case in which it is determined, based on the detection result signal received via the communication unit, that the detection unit included in a first number or more of the radiographic imaging devices among the plural radiographic imaging devices has detected the start of the application of the radiation, the first number being a predetermined positive integer.

In the above-described configuration, the control unit may be further configured to effect control of continuing accumulation of the charges generated by the sensor portions in at least one case of: (a) a case in which the determination unit included in a second number or more of the plural radiographic imaging devices has determined that noise is not superimposed, the second number being a predetermined positive integer, or (b) a case in which the determination unit included in a third number or more of the radiographic imaging devices, in which the start of the application of the radiation has been detected by the detection unit, has determined that noise is not superimposed, the third number being a predetermined positive integer.

In the above-described configuration, the control unit may be further configured to effect control of discontinuing accumulation of the charges generated by the sensor portions in at least one case of: (c) a case in which the determination units included in all of the plural radiographic imaging devices, connected to the communication unit, have determined that noise is superimposed, or (d) a case in which the determination units included in all of the radiographic imaging devices, in which the start of the application of the radiation has been detected by the detection units, have determined that noise is superimposed.

In the above-described configuration, the control unit may be further configured to release the charges accumulated in the sensor portions after discontinuing accumulation of the charges generated by the sensor portions, and the detection unit may be further configured to detect whether or not the application of the radiation has been started again with respect to the radiation detector.

In the first aspect, the plural radiographic imaging devices may be housed in a single casing. In the first aspect, the sensors that detect the radiation may also be housed in the casing.

In the first aspect, the detection unit may be further configured to detect whether or not the application of the radiation has been started based on whether or not the electrical signals satisfy a preset condition.

A second aspect of the present invention is a radiation detector including plural pixels, each of the pixels including a sensor portion that generates a charge corresponding to an amount of applied radiation and accumulates the generated charge, and a switch element for reading out the charge from the sensor portion; a detection unit configured to detect whether or not application of the radiation has been started with respect to the radiation detector based on electrical signals indicating detection results of sensors that detect application of the radiation and that are disposed in correspondence to the radiation detector; a determination unit configured to determine whether or not noise is superimposed on the electrical signal after the detection unit has detected whether or not the application of the radiation has been started with respect to the radiation detector; and a communication unit that is connected to another radiographic imaging device, which images a same subject with same applied radiation, and transmits to and receives from the other connected radiographic imaging device a detection result signal indicating the detection result of the detection unit and a determination result signal indicating the determination result of the determination unit.

A third aspect of the present invention is a method of controlling radiographic imaging devices in a radiographic imaging system including plural radiographic imaging devices that image a same subject with same applied radiation and are connected to one another via communication units, each of the plural radiographic imaging devices including a radiation detector in which plural pixels are disposed, and each of the pixels including a sensor portion that generates a charge corresponding to an amount of the applied radiation and accumulates the generated charge, and a switch element for reading out the charge from the sensor portion, the method including: detecting whether or not the application of the radiation has been started with respect to the radiation detector based on electrical signals indicating detection results of sensors that detect application of the radiation and that are disposed in correspondence to the radiation detector; determining whether or not noise is superimposed on the electrical signals after detecting whether or not the application of the radiation has been started with respect to the radiation detector; and transmitting to and receiving from another connected radiographic imaging device a detection result signal indicating the detection result and a determination result signal indicating the determination result.

In the third aspect, the detection result signal and the determination result signal may be binary signals.

A fourth aspect of the present invention is a non-transitory storage medium storing a program that causes a computer to execute processing for controlling each of radiographic imaging devices in a radiographic imaging system in which plural radiographic imaging devices are connected to one another, the processing including: detecting whether or not application of radiation has been started with respect to a radiation detector of the radiographic imaging device on the basis of electrical signals indicating detection results of sensors that detect the application of the radiation and that are disposed in correspondence to the radiation detector; determining whether or not noise is superimposed on the electrical signals after detecting whether or not the application of the radiation has been started with respect to the radiation detector; and transmitting to and receiving from another connected radiographic imaging device a detection result signal indicating the detection result and a determination result signal indicating a the determination result.

According to the above aspects, the trackability of incident radiation may be improved in a radiographic imaging system equipped with plural radiographic imaging devices that independently detect the start of application of radiation and perform imaging operations.

BRIEF DESCRIPTION OF THE DRAWINGS

Exemplary embodiments will be described in detail based on the following figures, wherein:

FIG. 7 illustrates graphs showing a temporal change in an electrical signal in a case in which noise has occurred in the radiation detector pertaining to the first embodiment, wherein graph (1) shows a temporal change in an electrical signal Di, graph (2) shows a temporal change in a first-order differential value Di1, and graph (3) shows a temporal change in a second-order differential value Di2;

DETAILED DESCRIPTION

First Embodiment

An example of the present embodiment will be described below with reference to the drawings.

Figure 1:
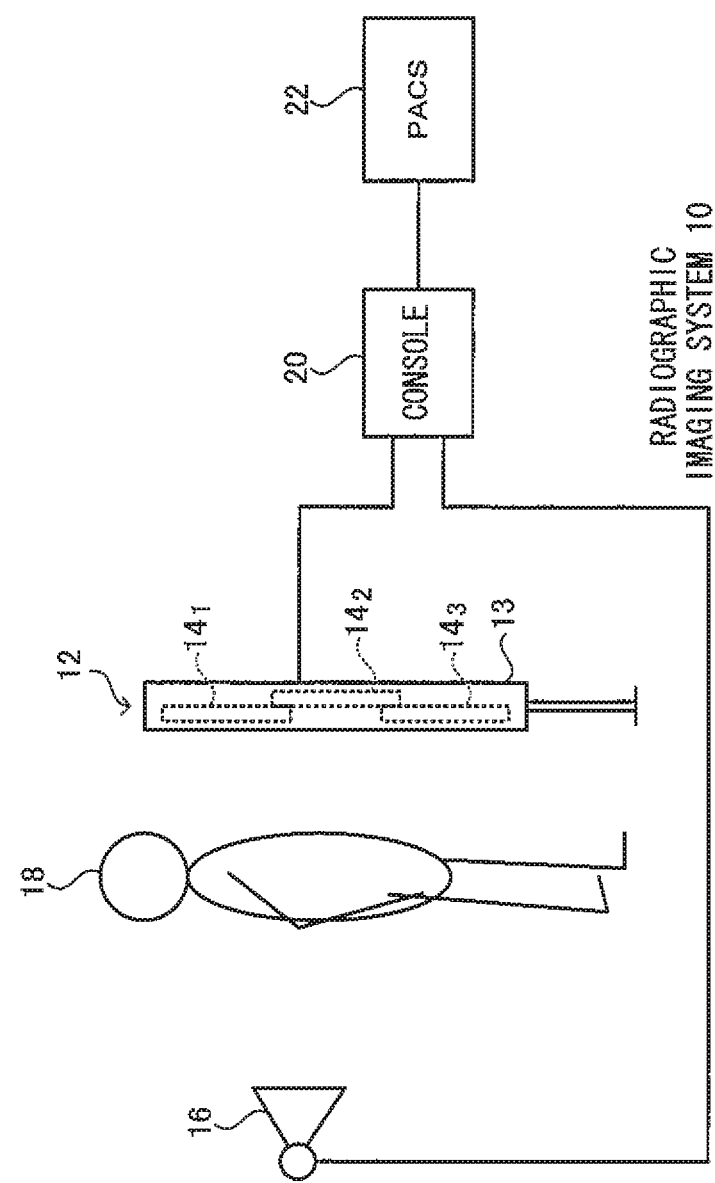
FIG. 1 is a diagram illustrating a schematic configuration of an example of a radiographic imaging system pertaining to a first embodiment.

First, the overall schematic configuration of a radiographic imaging system equipped with radiographic imaging devices of the present embodiment will be described. FIG. 1 is a schematic configuration diagram illustrating the overall configuration of an example of a radiographic imaging system 10 of the present embodiment. The radiographic imaging system 10 includes an electronic cassette 12 equipped with plural radiographic imaging devices 14 (e.g., $14_1$, $14_2$, and $14_3$). Each of the radiographic imaging devices 14 has a function of detecting the start of application of radiation (i.e., the start of imaging).

The radiographic imaging system 10 performs radiographic imaging when it is operated by a doctor or a radiologic technologist based on instructions (an imaging menu) that have been input from an external system such as a radiology information system (RIS), for example, via a console 20.

The radiographic imaging system 10 also allows a doctor or a radiologic technologist to read a radiographic image by displaying the radiographic image that has been captured by the electronic cassette 12 on a display (not illustrated in the drawings) of the console 20 or a radiographic image reading device (not illustrated in the drawings). The non-illustrated radiographic image reading device is not particularly limited, and may be any device having a function of allowing a reader to read captured radiographic images. Examples thereof include image viewers, displays, portable terminals, and tablet computers.

The radiographic imaging system 10 is equipped with the electronic cassette 12, a radiation application device 16, and the console 20.

The radiation application device 16 applies radiation from a radiation application source (not illustrated in the drawings) to an imaging target region of a subject 18 under control by the console 20.

The radiation that has passed through the subject 18 is applied to the electronic cassette 12. The radiographic imaging devices 14 of the electronic cassette 12 generates charges corresponding to the amount of radiation that has passed through the subject 18, creates image information (data) representing a radiographic image based on the generated charge amount, and outputs the image data. The electronic cassette 12 has plural radiographic imaging devices 14 inside a casing 13 (details described later).

In the present embodiment, the image data representing the radiographic image that has been output by the electronic cassette 12 is input to the console 20. The console 20 controls the electronic cassette 12 and the radiation application device 16 using the imaging menu and various types of information (data) acquired from the external system via a wireless local area network (LAN) or the like. The console 20 also transmits various types of information (data) to, and receives various types of information from, the electronic cassette 12. The console 20 outputs the radiographic image acquired from the electronic cassette 12 to a picture archiving and communication system (PACS) 22. The radiographic image imaged by the electronic cassette 12 is managed by the PACS 22.

The console 20 is configured as a server computer and is equipped with a control unit, a display driver, a display, an operation panel, an input/output (I/O) unit, and an interface (I/F) unit (none of which are illustrated in the drawings).

The control unit of the console 20 controls the operations of the entire console 20 and is equipped with a central processing unit (CPU), a read-only memory (ROM), a random access memory (RAM), and a hard disk drive (HDD). The CPU controls the operations of the entire console 20, and various programs including a control program used by the CPU are stored in advance in the ROM. The RAM temporarily stores various data, and the HDD stores and retains various data.

The display of the console 20 displays, under control of the display driver, imaging menus and captured radiographic images. The operation panel of the console 20 is provided for allowing a doctor or a radiologic technologist to input operation instructions relating to radiographic imaging and includes, for example, a touch panel, a touch pen, plural keys, and a mouse.

The I/O unit and the I/F unit of the console 20 transmits various types of information (data) to, and receives various types of information from, the electronic cassette 12, the radiation application device 16, and the PACS 22 by at least one of wireless communication or wired communication.

Next, the schematic configuration of the electronic cassette 12 of the present embodiment will be described. The electronic cassette 12 is equipped with the plural radiographic imaging devices 14. In the present embodiment, as a specific example, a case will be described in which, the electronic cassette 12 is equipped with three radiographic imaging devices 14 ($14_1$, $14_2$, and $14_3$) as illustrated in FIG. 1. However, the number of radiographic imaging devices 14 is not limited to this. Since the radiographic imaging devices $14_1$ to $14_3$ have the same configuration, they will be called "the radiographic imaging device(s) 14" when they are generically referred to, and when they are individually referred to, subscript numbers 1, 2, and 3 indicating each will be added after "14".

The three radiographic imaging devices 14 are housed inside the casing 13. As illustrated in FIG. 1, in the present embodiment, the radiographic imaging devices 14 are disposed adjacent to one another with the imaging plane facing the subject 18. In the electronic cassette 12, as illustrated in FIG. 1, the radiographic imaging devices 14 are disposed with their end portions overlying those of the adjacent radiographic imaging devices 14, but the configuration of the electronic cassette 12 is not limited to this. In the present embodiment, the radiographic imaging devices 14 are disposed with their end portions overlying one another as illustrated in FIG. 1 so that no spaces form in the imaging plane in order to suppress imaging omissions of the imaging region of the subject 18, but in a case in which no spaces will form in the imaging plane, the end portions of the radiographic imaging devices 14 do not have to overlie one another.

By disposing the plural (three) radiographic imaging devices 14 in this way, the electronic cassette 12 overall provides an elongated imaging plane.

Figure 2:
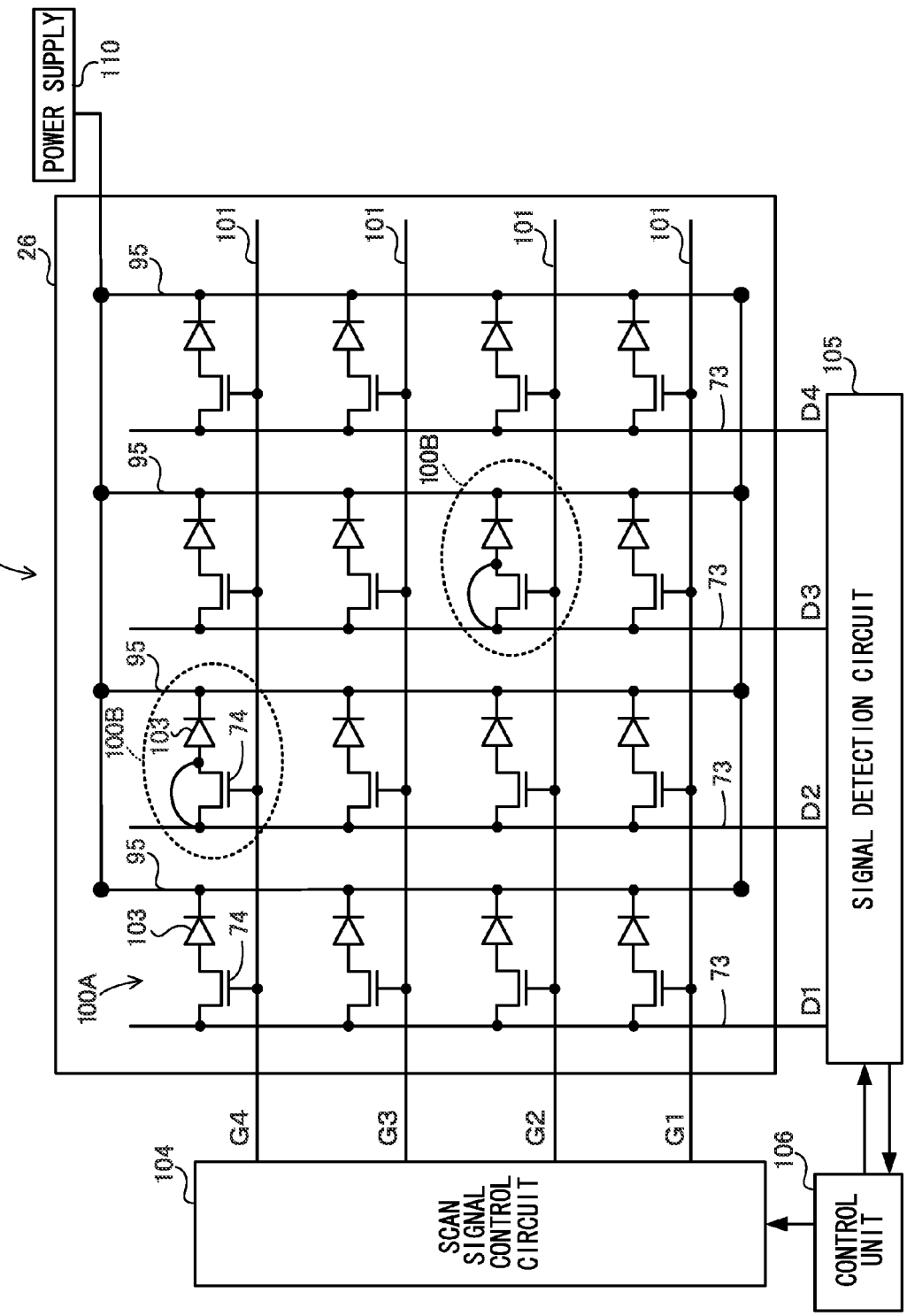
FIG. 2 is a diagram illustrating an example of a configuration of a radiographic imaging device pertaining to the first embodiment.

FIG. 2 is a configuration diagram illustrating an example of a configuration of the radiographic imaging device 14 pertaining to the present embodiment. In the present embodiment, a case will be described in which an indirect conversion type radiographic imaging device 14, which first converts radiation such as X-rays into light and then converts the light into charges, is adopted. In FIG. 2, a scintillator that converts the radiation into light is not illustrated.

A radiation detector 26 of the radiographic imaging device 14 includes pixels 100. Each of the pixels 100 includes a sensor portion 103, which receives the light, generates a charge, and accumulates the generated charge, and a thin-film transistor (TFT) switch 74, which is a switch element for reading out the charge accumulated in the sensor portion 103. In the present embodiment, the charges are generated in the sensor portions 103 as a result of the light into which the radiation has been converted by the scintillator being applied thereto.

The pixels 100 are plurally arranged in a matrix form in one direction (a gate line direction in FIG. 2) and an intersecting direction (a signal line direction in FIG. 2) intersecting the gate line direction. FIG. 2 illustrates a simplified array of the pixels 100, but, for example, the pixels 100 are arranged in an array of 1024×1024 pixels in the gate line direction and the signal line direction.

In the present embodiment, radiographic imaging pixels 100A and radiation detection pixels 100B functioning as an example of sensors that detect the radiation are determined in advance among the plural pixels 100. In FIG. 2, the radiation detection pixels 100B are encircled by dashed lines. The radiographic imaging pixels 100A are used to detect the radiation and create an image expressed by the radiation. The radiation detection pixels 100B are used in radiation detection for detecting the start of the application of the radiation and output charges even during the charge accumulation period (details described later).

Figure 3:
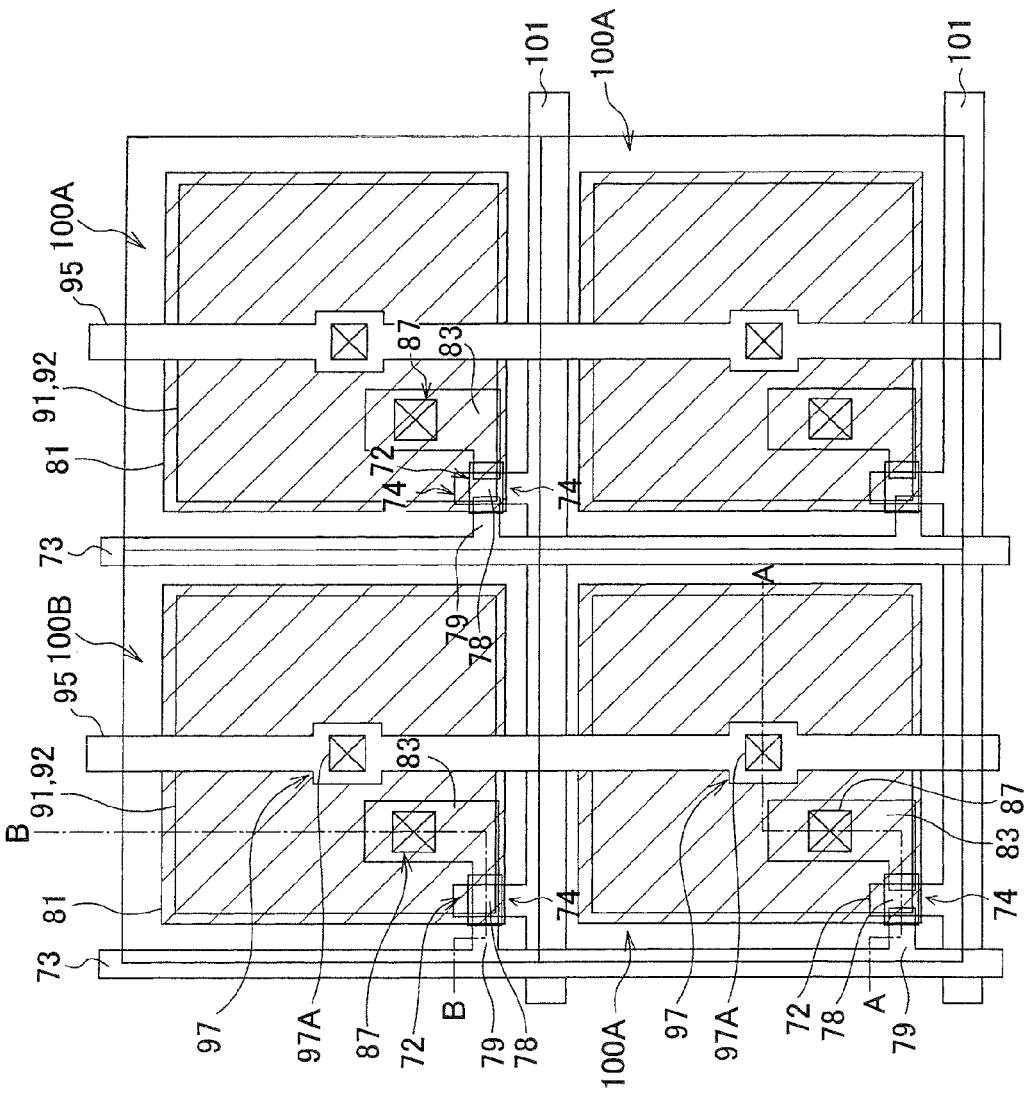
FIG. 3 is a plan view illustrating an example of a configuration of a radiation detector pertaining to the first embodiment.
Figure 4:
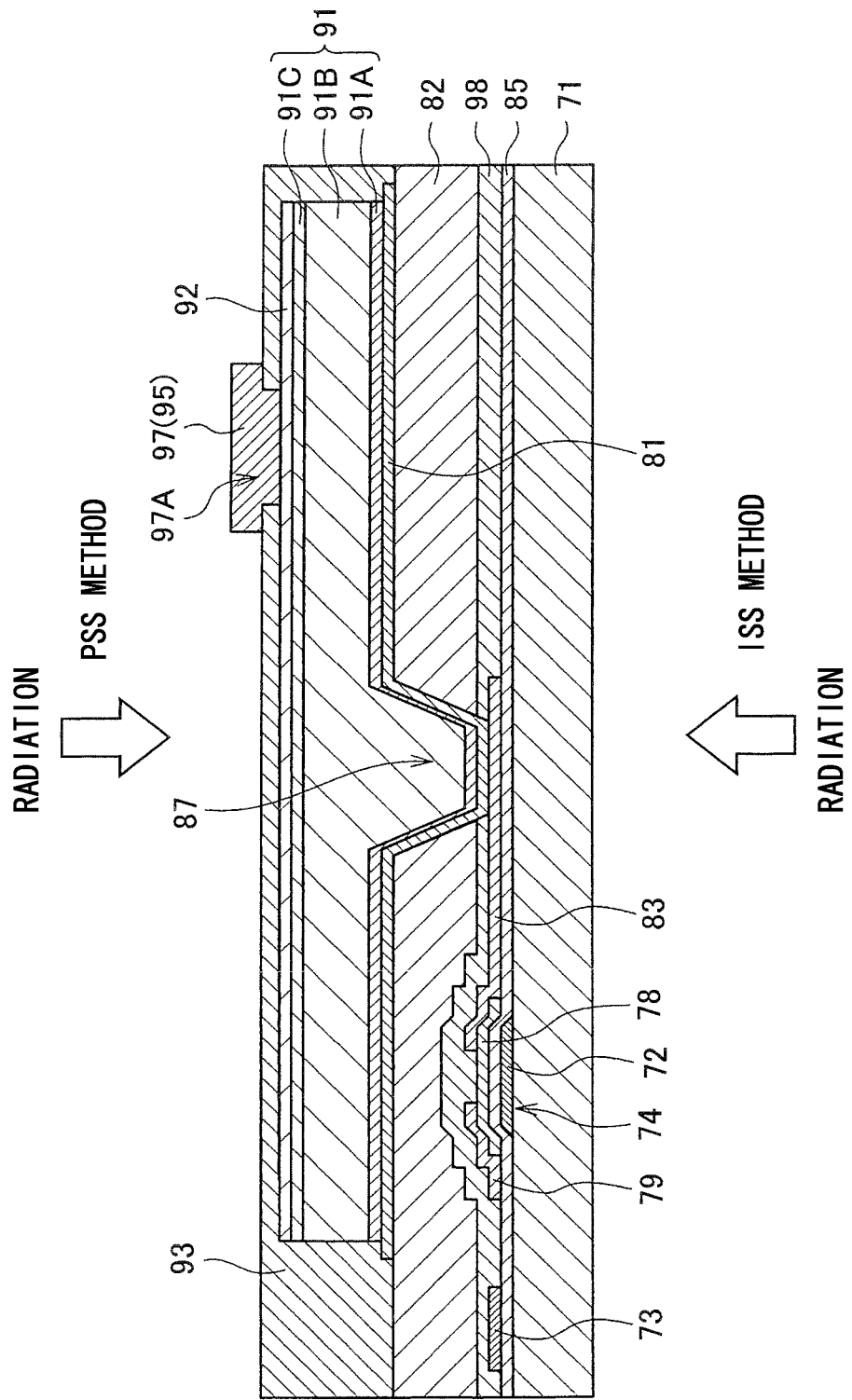
FIG. 4 is a sectional view, taken along line A-A of FIG. 3, of an example of the radiation detector pertaining to the first embodiment.
Figure 5:
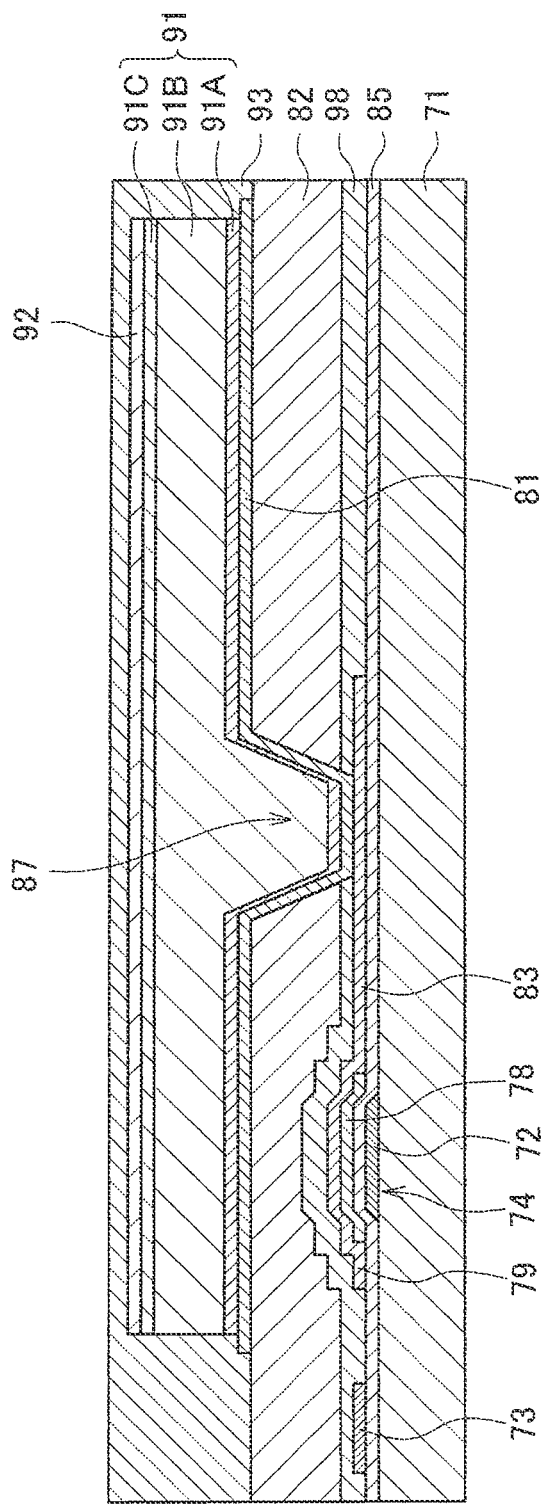
FIG. 5 is a sectional view, taken along line B-B of FIG. 3, of an example of the radiation detector pertaining to the first embodiment.

FIG. 3 is a plan view illustrating an example of the structure of the indirect conversion type radiation detector 26 pertaining to the present embodiment. FIG. 4 is a sectional view, taken along line A-A of FIG. 3, of one of the radiographic imaging pixels 100A. FIG. 5 is a sectional view, taken along line B-B of FIG. 3, of one of the radiation detection pixels 100B.

As illustrated in FIG. 4, in each of the pixels 100A of the radiation detector 26, a gate line 101 (see FIG. 3) and a gate electrode 72 are formed on an insulating substrate 71 formed by alkali-free glass, for example. The gate line 101 and the gate electrode 72 are connected to one another (see FIG. 3). The wiring layer in which the gate line 101 and the gate electrode 72 are formed (hereinafter this wiring layer will also be called a "first signal line layer") is formed using Al or Cu or a laminate film whose main constituent is Al or Cu, but the configuration of the wiring layer is not particularly limited to this.

An insulating film 85 is formed on the entire surface of the first signal line layer. The region of the insulating film 85 positioned over the gate electrode 72 acts as a gate insulating film in the TFT switch 74. The insulating film 85 contains SiNx, for example, and is formed by chemical vapor deposition (CVD).

A semiconductor active layer 78 is formed in an island form over the gate electrode 72 on the insulating film 85. The semiconductor active layer 78 is the channel portion of the TFT switch 74 and is formed by an amorphous silicon film, for example.

A source electrode 79 and a drain electrode 83 are formed above the insulating film 85. In the wiring layer in which the source electrode 79 and the drain electrode 83 are formed, a signal line 73 is formed together with the source electrode 79 and the drain electrode 83. The source electrode 79 is connected to the signal line 73 (see FIG. 3). The wiring layer in which the source electrode 79, the drain electrode 83, and the signal line 73 are formed (hereinafter this wiring layer will also be called a "second signal line layer") is formed using Al or Cu laminate film, or a laminate film whose main constituent is Al or Cu, but the configuration of the wiring layer is not particularly limited to this. An impurity-doped semiconductor layer (not illustrated in the drawings) configured by impurity-doped amorphous silicon, for example, is formed between the source electrode 79 and drain electrode 83 and the semiconductor active layer 78. The TFT switch 74 for switching is configured by these layers and components. The source electrode 79 and the drain electrode 83 of the TFT switch 74 may be reversed due to the polarity of the charge collected and accumulated by a later-described lower electrode 81.

Covering the second signal line layer, on substantially the entire surface of the region (substantially the entire region) on the substrate 71 where the pixel 100 is disposed, a TFT protective film layer 98 is formed in order to protect the TFT switch 74 and the signal line 73. The TFT protective film layer 98 contains SiNx, for example, and is formed by CVD, for example.

A coated interlayer insulating film 82 is formed on the TFT protective film layer 98. The interlayer insulating film 82 is formed having a film thickness of 1 to 4 μm by a low-permittivity (having a relative permittivity $\epsilon_r$=2 to 4) photosensitive organic material (e.g., a positive-acting photosensitive acrylic resin, a material in which a positive-acting naphthoquinone diazide photosensitizer is mixed together with a base polymer formed by a copolymer of methacrylic acid and glycidyl methacrylate).

In the radiation detector 26 pertaining to the present embodiment, the capacitance between metals disposed above and below the interlayer insulating film 82 is kept low due to the interlayer insulating film 82. Usually the material used as the interlayer insulating film 82 also has a function as a planarizing film and also has an effect of smoothing out differences in the height of the underlying layer. In the radiation detector 26, a contact hole 87 is formed in the interlayer insulating film 82 and the TFT protective film layer 98 in a position opposing the drain electrode 83.

On the interlayer insulating film 82, a lower electrode 81 of the sensor portion 103 is formed in a manner so as to fill the contact hole 87 and cover the pixel region. The lower electrode 81 is connected to the drain electrode 83 of the TFT switch 74. There are virtually no restrictions on the material used for the lower electrode 81 provided that the material is conductive in a case in which a later-described semiconductor layer 91 has a thickness of around 1 μm. For this reason, there is no problem if the lower electrode 81 is formed using a conductive metal such as an Al material or indium tin oxide (ITO).

However, in a case in which the film thickness of the semiconductor layer 91 is thin (around 0.2 to 0.5 μm), since light absorption by the semiconductor layer 91 is insufficient, in order to prevent an increase in leak current caused by the application of light to the TFT switch 74, it is preferable for the lower electrode 81 to contain an alloy or a laminate film whose main constituent is a light-blocking metal.

On the lower electrode 81, a semiconductor layer 91 that functions as a photodiode is formed. In the present embodiment, a photodiode having a PIN structure formed by laminating an n+ layer, an i layer, and a p+ layer (n+ amorphous silicon, amorphous silicon, and p+ amorphous silicon) is used as the semiconductor layer 91. The semiconductor layer 91 is formed by successively laminating an n+ layer 91, an i layer 91B, and a p+ layer 91C from the lower layer. The i layer 91B generates a charge (a free electron and a free hole pair) when light is applied thereto. The n+ layer 91A and the p+ layer 91C function as contact layers and electrically connect the i layer 91B to the lower electrode 81 and a later-described upper electrode 92, respectively.

On each of the semiconductor layers 91, an upper electrode 92 is individually formed. A highly light-transmitting material such as ITO or indium zinc oxide (IZO), for example, is used for the upper electrode 92. In the radiation detector 26 pertaining to the present embodiment, the sensor portion 103 are configured to include the upper electrode 92, the semiconductor layer 91, and the lower electrode 81.

On the interlayer insulating film 82, the semiconductor layers 91, and the upper electrodes 92, a coated interlayer insulating film 93 is formed in a manner so as to cover each of the semiconductor layers 91 and have openings 97A in the parts corresponding to the upper electrodes 92.

On the interlayer insulating film 93, common electrode lines 95 are formed by Al or Cu or an alloy or laminate film whose main constituent is Al or Cu. The common electrode lines 95 have contact pads 97 formed thereon near the openings 97A and are electrically connected to the upper electrodes 92 via the openings 97A in the interlayer insulating film 93.

Turning now to the radiation detection pixels 100B of the radiation detector 26, as illustrated in FIG. 5, the TFT switch 74 is formed with the source electrode 79 and the drain electrode 83 in contact with one another. That is, in the pixels 100B, the source and drain of the TFT switch 74 are shorted. Consequently, in the pixels 100B, the charges collected in the lower electrodes 81 flow out to the signal lines 73 regardless of the switching state of the TFT switches 74.

On the radiation detector 26, a protective film is formed as needed using a low light-absorbing insulating material, and the scintillator that is a radiation conversion layer is adhered to the surface using a low light-absorbing adhesive resin. Or, the scintillator may be formed by vacuum deposition. As the scintillator, a scintillator that generates fluorescent light having a relatively wide wavelength range, and which is able to generate light with an absorbable wavelength range, is preferred. Examples of scintillators include CsI:Na, CaWO$_4$, YTaO$_4$:Nb, BaFX:Eu (X is Br or Cl), or LaOBr:Tm and GOS. Specifically, in a case of performing imaging using X-rays as the radiation, a scintillator including cesium iodide (CsI) is preferable, and it is particularly preferable to use CsI:Ti (cesium iodide doped with thallium) or CsI:Na whose emission spectrum when X-rays are applied is 400 nm to 700 nm. The emission peak wavelength in the visible light range of CsI:Ti is 565 nm. In a case of using a scintillator including CsI as the scintillator, it is preferable to use a scintillator formed as a rectangular columnar crystal structure by vacuum deposition.

As illustrated in FIG. 4, in a case in which a penetration side sampling (PSS) method is adopted to the radiation detector 26, i.e., the radiation is applied from the side on which the semiconductor layer 91 is formed and the radiographic image is read by the TFT substrate disposed on the back side of the surface on which the radiation is made incident, light is more strongly emitted by the upper side in FIG. 4 of the scintillator that is disposed on the semiconductor layer 91. In contrast, in a case in which an irradiation side sampling (ISS) method is adopted to the radiation detector 26, i.e., the radiation is applied from the TFT substrate side and the radiographic image is read by the TFT substrate disposed on the front side of the surface on which the radiation is made incident, the radiation that has passed through the TFT substrate is made incident on the scintillator and the TFT substrate side of the scintillator emits light more strongly. Charges are generated at the sensor portion 103 of each of the pixels 100 disposed on the TFT substrate, due to the light generated by the scintillator. Since the light emission position of the scintillator relative to the TFT substrate is closer in the radiation detector 26 adapted to the irradiation side sampling method than in the radiation detector 26 adapted to the penetration side sampling method, the resolution of the radiographic image obtained by the imaging is higher in the radiation detector 26 adapted to the irradiation side sampling method.

The radiation detector 26 is not limited to the configuration illustrated in FIG. 3 to FIG. 5 and may be modified in a variety of ways. For example, in the case of adopting the penetration side sampling method, the potential for the radiation to arrive is low, instead of the above described configuration, other imaging elements such as complementary metal-oxide semiconductor (CMOS) image sensors, whose tolerance to radiation is low, and TFTs may also be combined. Or, charge-coupled device (CCD) image sensors that shift and transfer charges using shift pulses corresponding to gate signals of TFTs may also be employed as the imaging elements.

Furthermore, for example, a flexible substrate may be used for the radiation detector 26. As the flexible substrate, it is preferable in terms of improving the transmittance of the radiation to apply a substrate that uses, as its base material, ultrathin glass made by the float process that has been developed in recent years. Ultrathin glass that can be applied in this case is disclosed online, for example, in "AGC Develops World's Thinnest Sheet Float Glass at Just 0.1 MM" (URL: https://www.agc.com/english/news/2011/0516e.pdf) (searched Aug. 20, 2011).

In the radiation detector 26, the plural gate lines 101 for switching on and off the TFT switches 74 and the plural signal lines 73 for reading out the charges accumulated in the sensor portions 103 are disposed intersecting one another on the substrate 71 (see FIG. 4). In the present embodiment, the signal lines 73 are disposed one for each pixel row in the one direction and the gate lines 101 are disposed one for each pixel row in the intersecting direction. For example, in a case in which the pixels 100 are arranged in an array of 1024×1024 pixels in the gate line direction and the signal line direction, there are 1024 lines of the signal lines 73 and 1024 lines of the gate lines 101.

The common electrode lines 95 are disposed in parallel with the signal lines 73 in the radiation detector 26. One end and the other end of each of the common electrode lines 95 are connected in parallel, with the one end of each of the common electrode lines 95 being connected to a power supply 110 that supplies a predetermined bias voltage. The sensor portions 103 are connected to the common electrode lines 95, and the bias voltage is applied to the sensor portions 103 via the common electrode lines 95.

Control signals for switching the TFT switches 74 through the gate lines 101. The TFT switches 74 are switched as a result of the control signals flowing through the gate lines 101.

Electrical signals corresponding to the charges accumulated in the pixels 100 flow through the signal lines 73 in accordance with the switching state of the TFT switches 74 of the pixels 100. More specifically, electrical signals corresponding to the amount of charge accumulated as a result of any of the TFT switches 74 of the pixels 100 connected to the signal lines 73 being switched on flow through the signal lines 73.

A signal detection circuit 105 that detects the electrical signals flowing through the signal lines 73 is connected to the signal lines 73. Furthermore, a scan signal control circuit 104 that outputs to the gate lines 101 the control signals for switching on and off the TFT switches 74 is connected to the gate lines 101. FIG. 2 simplistically illustrates one signal detection circuit 105 and one scan signal control circuit 104. However, for example, plural signal detection circuit 105 and plural scan signal control circuit 104 may be provided and a predetermined number (e.g., 256 lines) of the signal lines 73 or the gate lines 101 may be connected to each of them. For example, in a case in which 1024 lines of the signal lines 73 and 1024 lines of the gate lines 101 are provided, four scan signal control circuits 104 may be provided and 256 gate lines 101 may be connected to each of the four scan signal control circuits 104, and four signal detection circuits 105 may also be provided and 256 signal lines 73 may be connected to each of the four signal detection circuits 105.

The signal detection circuit 105 includes, for each of the signal lines 73, amplifier circuits (not illustrated in the drawings) that amplify the input electrical signals. In the signal detection circuit 105, the electrical signals input from the signal lines 73 are amplified by the amplifier circuits and are converted into digital signals by analog-to-digital converters (ADC).

A control unit 106 is connected to the signal detection circuit 105 and the scan signal control circuit 104. The control unit 106 performs predetermined processing such as denoising on the digital signals into which the electrical signals have been converted in the signal detection circuit 105, outputs control signals indicating signal detection timings to the signal detection circuit 105, and outputs control signals indicating scan signal output timings to the scan signal control circuit 104.

Figure 9:
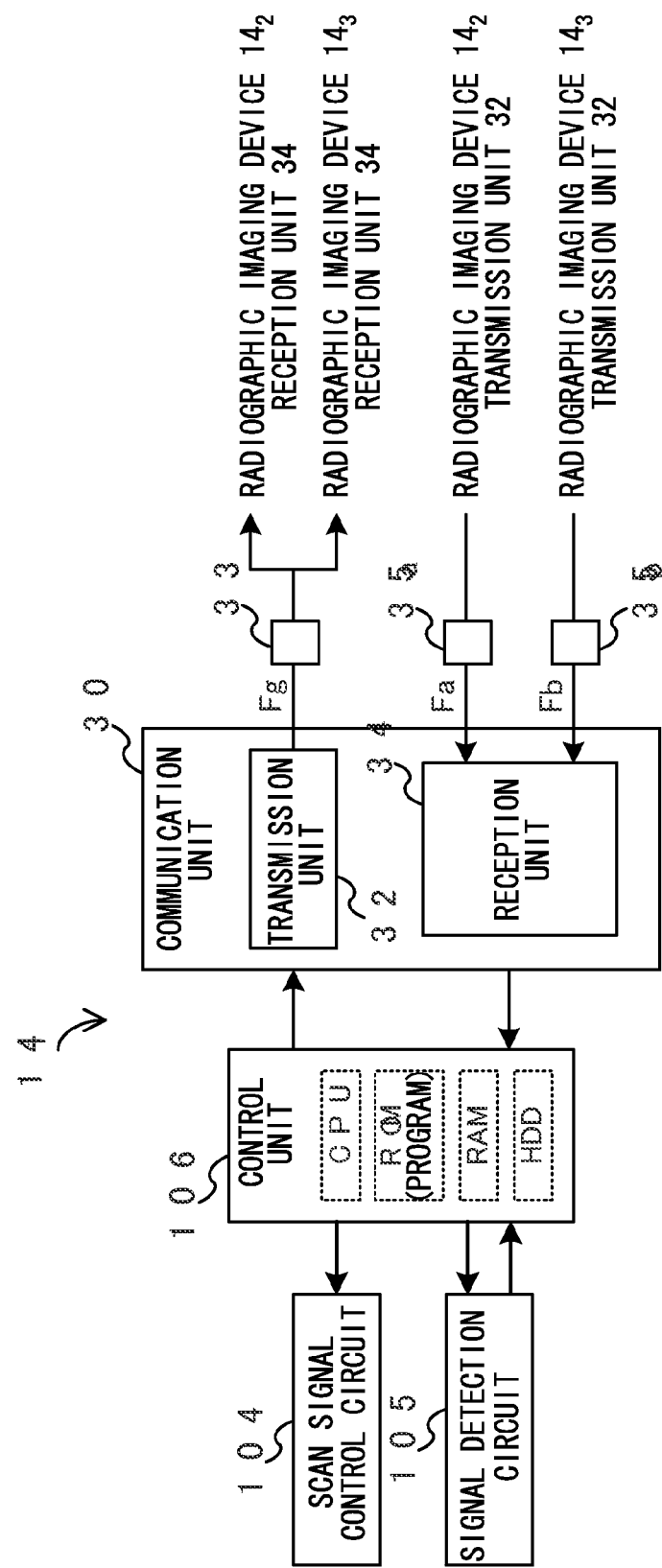
FIG. 9 is a schematic configuration diagram describing an exemplary configuration of a function of communicating a detection result and a determination result to other radiographic imaging devices to which the radiographic imaging device pertaining to the first embodiment is connected.

The control unit 106 of the present embodiment is a microcomputer and is equipped with a CPU, a ROM, a RAM, and a HDD (see FIG. 9). The control unit 106 performs control for radiographic imaging by executing in the CPU a program stored in the ROM. The control unit 106 also performs, on the image data on which the aforementioned predetermined processing has been performed, processing (interpolation processing) that interpolates the image data of the radiation detection pixels 100B to thereby generate an image represented by the applied radiation. That is, the control unit 106 generates an image represented by the applied radiation by interpolating, on the basis of the image data on which the aforementioned predetermined processing has been performed, the image data of the radiation detection pixels 100B.

Furthermore, the control unit 106 functions as a detection unit that detects the start of the application of the radiation by the radiation application device 16 with respect to the radiation detector 26, and as a determination unit that determines whether or not noise is superimposed (occurring).

First, a case will be described where the control unit 106 functions as a detection unit that detects the start of the application of the radiation. The electrical signal (charge information) of a signal line 73 (in the case of FIG. 2, at least one of D2 and D3; for example, D2) to which a radiation detection pixel 100B is connected is detected by an amplifier circuit of the signal detection circuit 105. The control unit 106 compares the value of the digital signal into which the electrical signal has been converted by the signal detection circuit 105 with a detection threshold value determined beforehand, and performs a detection as to whether or not the radiation has been applied based on whether or not the value of the digital signal is equal to or greater than the threshold value, i.e., performs the detection relating to the application of the radiation without requiring a control signal from an external system such as the console 20. The detection by the control unit 106 as to whether or not the radiation has been applied is not limited to a comparison with a detection threshold value and may also, for example, be performed on the basis of a preset condition such as the number of detections.

The "detection" of the electrical signal in the present embodiment means sampling the electrical signal.

Next, a case will be described where the control unit 106 functions as a determination unit that determines whether or not noise is occurring. Specifically, the control unit 106 determines whether or not electrical signals generated by noise are superimposed on the electrical signals output from the radiation detection pixels 100B by determining whether or not noise is occurring.

When imaging the subject 18 as an imaging subject, there are cases in which noise (charges) occurs in the sensor portions 103 due to a disturbance such as an impact, electromagnetic waves, and particularly vibration. An electrical signal (charge information) corresponding to noise (charges) that has occurred due to a disturbance has characteristics that differ from those of an electrical signal (charge information) corresponding to charges generated as a result of radiation application during normal radiographic imaging, and in particular its temporal change is different. For example, in a case in which the electrical signal is noise, there are cases in which the polarity of the electrical signal is the opposite to normal as a result of the charges reversely flowing. Furthermore, in a case in which the electrical signal is noise, the waveform representing the temporal change in the electrical signal has an amplitude.

Figure 6:
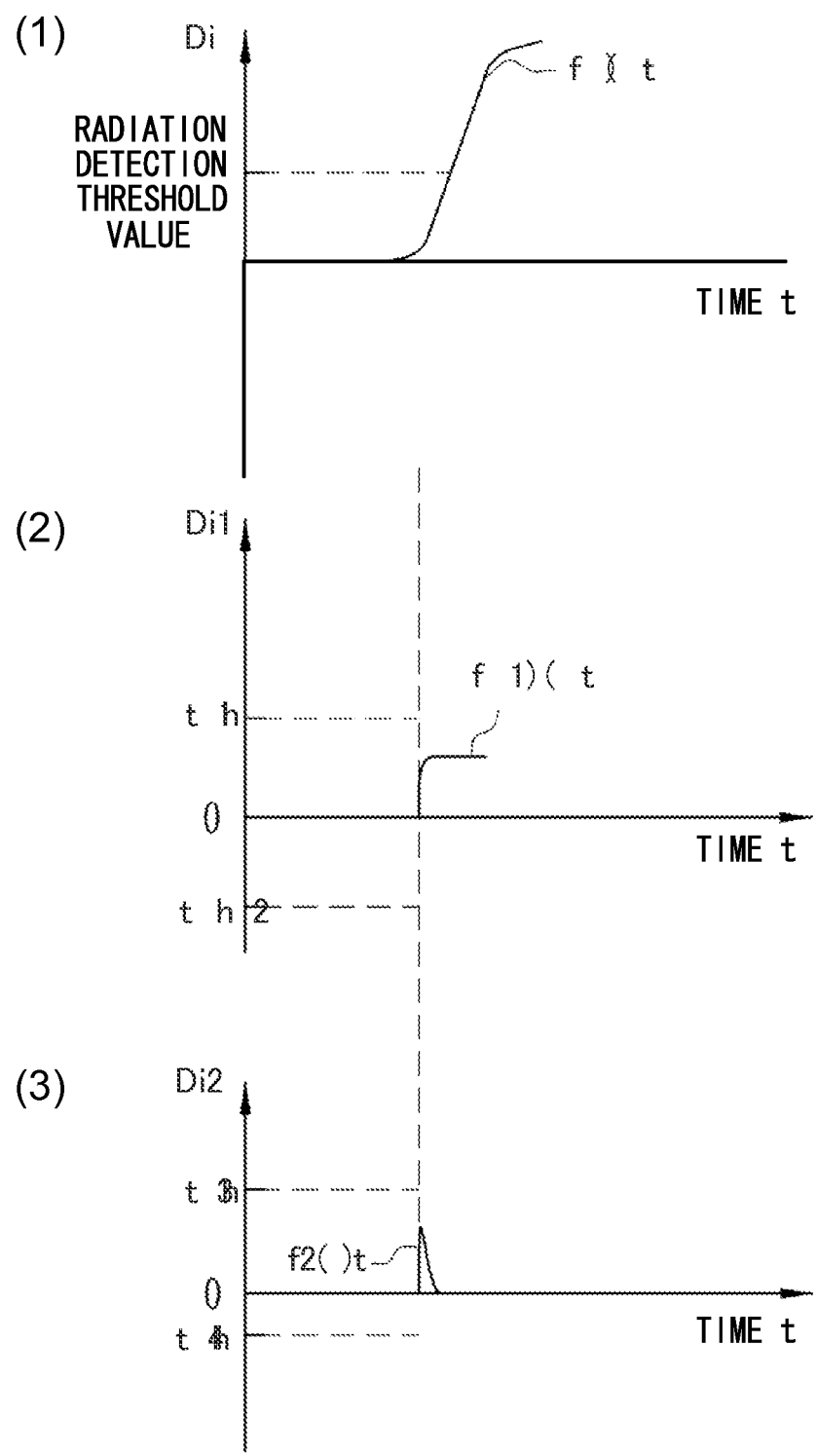
FIG. 6 illustrates graphs showing a temporal change in an electrical signal in a case in which radiation has been applied to the radiation detector pertaining to the first embodiment, wherein graph (1) shows a temporal change in an electrical signal Di, graph (2) shows a temporal change in a first-order differential value Di1, and graph (3) shows a temporal change in a second-order differential value Di2.

The difference between an electrical signal resulting from the application of the radiation in the radiation detector 26 and an electrical signal resulting from noise will be described in greater detail. FIG. 6 illustrates graphs of a temporal change in an electrical signal in a case in which radiation has been applied to the radiation detector 26 pertaining to the present embodiment. Graph (1) of FIG. 6 show a temporal change in an electrical signal Di, graph (2) shows a temporal change in a first-order differential value Di1 of the electrical signal Di, and graph (3) shows a temporal change in a second-order differential value Di2 of the electrical signal Di. FIG. 7 illustrates graphs of a temporal change in an electrical signal in a case in which noise has occurred in the radiation detector 26 pertaining to the present embodiment. Graph (1) of FIG. 7 shows a temporal change in an electrical signal Di, graph (2) shows a temporal change in a first-order differential value Di1 of the electrical signal Di, and graph (3) shows a temporal change in a second-order differential value Di2 of the electrical signal Di.

As shown in graph (1) of FIG., when the radiation is applied, since the electrical signal Di increases and changes over time, the temporal change can be expressed as a function f(t) of time t. In the radiation detector 26 of the present embodiment, the control unit 106 detects the start of the application of the radiation based on whether or not the electrical signal Di has exceeded a detection threshold value. In graph (1) of FIG. 7, the electrical signal Di generated by noise changes over time in the same way as the electrical signal Di in the case in which the radiation has been applied, and the temporal change can also be expressed as a function g(t) of time t. However, in this case the electrical signal is a sine wave whose period is constant and whose amplitude gradually decreases, which is to say the electrical signal has a damped oscillatory waveform. When the electrical signal is subjected to first-order differentiation, as shown in graph (2) of FIG. 7, a waveform g1($t$) whose phase is 90° different is obtained.

As shown in graph (2) of FIG. 6, the first-order differential f1($t$) of the function f(t) in the case in which the radiation has been applied rises abruptly because of the application of the radiation and soon becomes constant. In contrast, in the first-order differential g1($t$) of the function g(t) of the waveform resulting from noise of graph (2) of FIG. 7, only the phase is shifted and the waveform of the damping signal does not change. In a case in which the radiation has truly been applied, the first-order differential f1($t$) always exhibits a positive polarity, but in the case resulting from noise, the first-order differential g1($t$) reverses polarity and has an amplitude that alternates between a positive polarity and a negative polarity.

Furthermore, as shown in graph (3) of FIG. 6, the second-order differential f2($t$) of the function f(t) in the case in which the radiation has been applied behaves like a Gaussian function. In contrast, in the second-order differential g2($t$) of the function g(t) of the waveform resulting from noise of graph (3) of FIG. 7, only the phase is shifted similarly to the case of the first-order differential and the waveform of the damping signal does not change. In this way, in the case of the second-order differential also, similarly to the first-order differential, in a case in which the radiation has truly been applied, the second-order differential f21($t$) always exhibits a positive polarity, but in the case resulting from noise, the second-order differential g2($t$) reverses polarity, exhibits a negative polarity, and has an amplitude that alternates between a positive polarity and a negative polarity.

As will be understood by comparing FIG. 6 and FIG. 7, the first-order differential f1($t$) in the case in which the radiation has been truly applied is smaller than the first-order differential g1($t$) in the case of noise. Similarly, the second-order differential f2($t$) in the case in which the radiation has been truly applied is smaller than the second-order differential g2($t$) in the case of noise. Therefore, noise judgment threshold values (th1, th2) for discriminating between the first-order differential f1($t$) and the first-order differential g1($t$) may be determined in advance, and the control unit 106 may judge that noise has occurred in a case in which the temporal change in the electrical signal has exceeded the noise judgment threshold values. Similarly, noise judgment threshold values (th3, th4) for discriminating between the second-order differential f2($t$) and the second-order differential g2(t) may be determined beforehand, and the control unit 106 may judge that noise has occurred in a case in which the temporal change in the electrical signal has exceeded the noise judgment threshold values.

In the present embodiment, the control unit 106 continues detecting the electrical signals output from the radiation detection pixels 100B even after detecting the start of the application of the radiation and judges whether or not noise has occurred based on whether or not the temporal change in the electrical signals in a predetermined detection period have the noise characteristic described above. Specifically, as described above, examples for such determination include determining based on whether or not the polarity of the electrical signals has become the opposite to the normal; determining based on whether or not the slope is decreasing, such as differentiating (e.g., first-order differentiation or second-order differentiation) the electrical signals that have been output in a predetermined detection period and judging that noise is not occurring in a case in which the slope can be regarded as being substantially constant or gradually increasing; and determining using noise judgment threshold values. In order to enhance the precision with which the control unit 106 detects the occurrence of noise, it is preferable to perform several types of judgments in combination.

Since the aforementioned predetermined detection period differs depending on the imaging conditions and the radiographic imaging devices 14, it is preferable to obtain the predetermined detection period by an experiment or the like in advance, for example, as a certain percentage of the accumulation period in which the charges corresponding to the applied radiation are accumulated by the pixels 100.

The noise that occurs may differ depending on the signal lines 73, such as charges being generated in a particular signal line 73 in a case in which the radiation detector 26 has received a strong impact as a disturbance. Or, the noise that occurs may differ depending on the region where the pixels 100 are disposed. In such cases, the noise that occurs in each of the signal lines 73 may be obtained in advance by an experiment or the like, and the judgment criteria may be varied in accordance with each of the signal lines 73. Alternatively, the region where the pixels 100 are disposed (the region where the radiation is applied) may be divided into plural regions, the noise that occurs may be obtained in advance by an experiment or the like for each divided region, and the judgment criteria may be varied in accordance with each of the regions. For example, the aforementioned noise judgment threshold values (th1 to th4) may be determined in advance in accordance with each of the signal lines 73 and each of the regions. In a case in which the judgment criteria are varied in accordance with the signal lines 73 or each of the regions, the control unit 106 may judge whether or not noise is occurring in each of the signal lines 73 or each of the regions. In a case in which the number of judgment results indicating that noise has occurred is equal to or greater than one, or equal to or greater than a predetermined number, the control unit 106 may determine that noise has occurred.

In the present embodiment, three radiographic imaging devices 14 are connected to one another, and the control unit 106 of each of the radiographic imaging devices 14 communicates to the other radiographic imaging devices 14 the detection result of the start of the application of the radiation and the determination result of whether or not noise has occurred.

Figure 8:
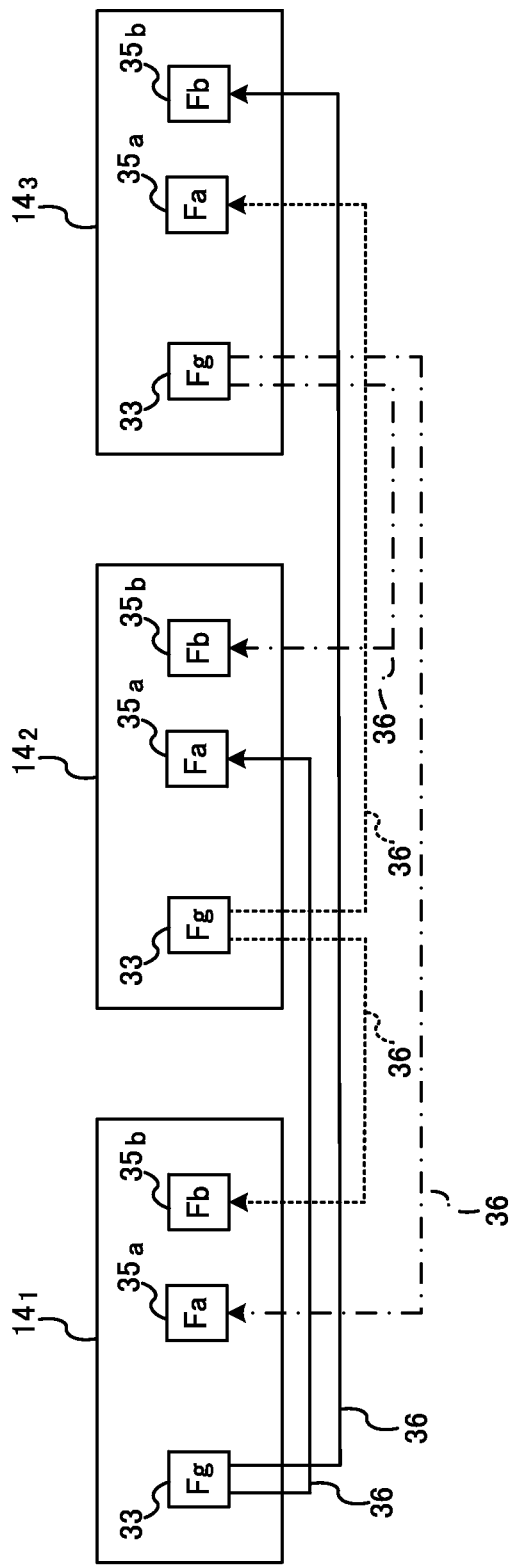
FIG. 8 is an explanatory drawing for describing an example of a connection relationship between three radiographic imaging devices pertaining to the first embodiment.

FIG. 8 is an explanatory drawing for describing an example of a connection relationship between the radiographic imaging devices 14$_1$ to 14$_3$.

As illustrated in FIG. 8, the three radiographic imaging devices 14 (14$_1$ to 14$_3$) are electrically connected in parallel to one another by wires. Because the radiographic imaging devices 14 are connected in parallel, each of the radiographic imaging devices 14 is equipped with one transmission terminal 33 and a number of reception terminals 35 (35*a* and 35*b*) equal to the number of radiographic imaging devices 14 included in the electronic cassette 12 minus one (in the present case, 3−1=2).

In the present embodiment, the transmission terminal 33 of the radiographic imaging device 14$_1$ is connected by signal wires 36 to the reception terminal 35*a* of the radiographic imaging device 14$_2$ and the reception terminal 35*b* of the radiographic imaging device 14$_3$. A transmission signal Fg transmitted from the transmission terminal 33 of the radiographic imaging device 14$_1$ is received as a reception signal Fa by the reception terminal 35*a* of the radiographic imaging device 14$_2$. The transmission signal Fg transmitted from the transmission terminal 33 of the radiographic imaging device 14$_1$ is received as a reception signal Fb by the reception terminal 35*b* of the radiographic imaging device 14$_3$.

In the present embodiment, flags Fx and Ft are internal signals of each device and are flags. The transmission signal Fg and the reception signals Fa and Fb are each signals defined by the flags Fx and Ft and have two types of states: a high level and a low level. In the present embodiment, the high level is assigned to "TRUE" and the low level is assigned to "FALSE".

Similarly, the transmission terminal 33 of the radiographic imaging device 14$_2$ is connected by signal wires 36 to the reception terminal 35*b* of the radiographic imaging device 14$_1$ and the reception terminal 35*a* of the radiographic imaging device 14$_3$. A transmission signal Fg transmitted from the transmission terminal 33 of the radiographic imaging device 14$_2$ is received as a reception signal Fb by the reception terminal 35*b* of the radiographic imaging device 14$_1$. The transmission signal Fg transmitted from the transmission terminal 33 of the radiographic imaging device 14$_2$ is received as a reception signal Fa by the reception terminal 35*a* of the radiographic imaging device 14$_3$.

The transmission terminal 33 of the radiographic imaging device 14$_3$ is connected by signal wires 36 to the reception terminal 35*a* of the radiographic imaging device 14$_1$ and the reception terminal 35*b* of the radiographic imaging device 14$_2$. A transmission signal Fg transmitted from the transmission terminal 33 of the radiographic imaging device 14$_3$ is received as a reception signal Fa by the reception terminal 35*a* of the radiographic imaging device 14$_1$. The transmission signal Fg transmitted from the transmission terminal 33 of the radiographic imaging device 14$_3$ is received as a reception signal Fb by the reception terminal 35*b* of the radiographic imaging device 14$_2$.

In the present embodiment, the signals (Fg, Fa, and Fb) communicated via communication units 30 between the radiographic imaging devices 14 are analog signals. For that reason, the signal wires 36 are preferably wires suited to communicating analog signals at a high speed. In the present embodiment, hard wires are used as a specific example.

FIG. 9 is a schematic configuration drawing illustrating an example of a configuration for describing the function of communicating the detection result and the determination result to the radiographic imaging devices 14$_2$ and 14$_3$ to which the radiographic imaging device $14_1$ pertaining to the present embodiment is connected.

As illustrated in FIG. 9, the radiographic imaging device 14 ($14_1$) is equipped with a communication unit 30. The communication unit 30 has both transmitting and receiving functions. The exemplary communication unit 30 includes a transmission unit 32 and a reception unit 34.

The transmission unit 32 transmits, to the other radiographic imaging devices 14 ($14_2$ and $14_3$) via the transmission terminal 33, a detection result signal indicating the detection result obtained by the control unit 106 and a determination result signal indicating the determination result of whether or not noise has occurred.

The reception unit 34 receives, via the reception terminals 35a and 35b, detection result signals and determination result signals transmitted from the transmission units 32 of the other radiographic imaging devices 14 ($14_2$ and $14_3$).

Figure 10:
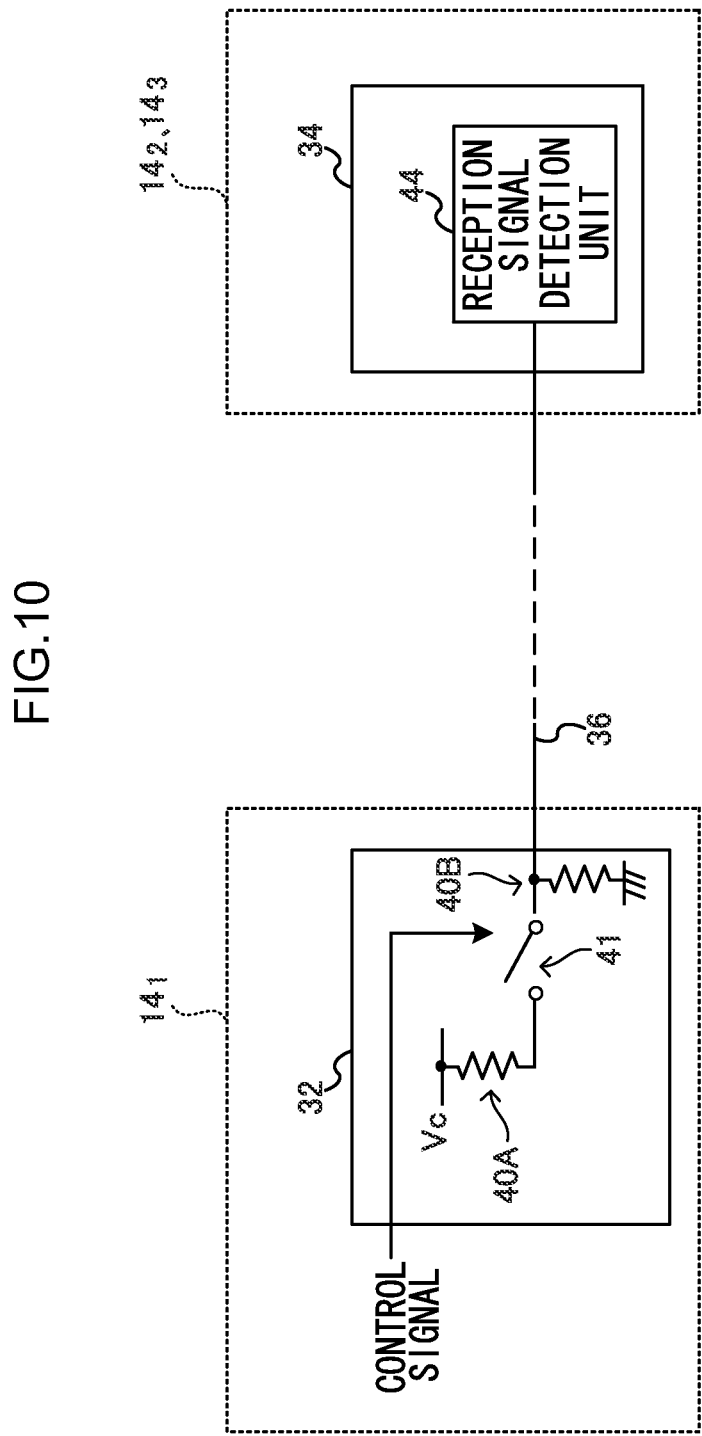
FIG. 10 is a schematic configuration diagram for describing an example of a transmission unit and a reception unit of the first embodiment.

FIG. 10 is a schematic configuration drawing for describing an example of the transmission unit 32 and the reception unit 34 of the present embodiment.

The transmission unit 32 is equipped with a buffer amp 40A, a resistor element 40B, and a switching element 41. A power supply such as a power supply line or a power supply unit disposed inside the radiographic imaging device 14 is connected to the input of the buffer amp 40A, and the switching element 41 is connected to the output of the buffer amp 40A. One end of the resistor element 40B is connected to a signal wire or the like (a ground as a specific example), to which a voltage corresponding to a low level that is a lower voltage than a voltage signal Vcc is applied, and the other end is connected to the switching element 41.

The control unit 106 outputs a control signal to the switching element 41 of the transmission unit 32 based on the detection result and the determination result. In the transmission unit 32, the switching on and off of the switching element 41 is controlled by the control signal input from the control unit 106. When the switching element 41 is switched on, the reception units 34 (reception signal detection units 44) of the other radiographic imaging devices 14 are connected by the signal wires 36 to the power supply via the buffer amp 40A. Because of this, a high-level (e.g., "1") transmission signal Fg corresponding to the potential of the voltage signal Vcc is transmitted from the transmission unit 32 of the radiographic imaging device 14. In a case in which the switching element 41 is off, the reception units 34 (the reception signal detection units 44) of the other radiographic imaging devices 14 are connected by the signal wires 36 to the ground via the resistor element 40B, and a low-level (e.g., "0") transmission signal Fg is transmitted.

The reception unit 34 of the present embodiment is equipped with the reception signal detection unit 44. The reception signal detection unit 44 interprets the received reception signals Fa and Fb. The reception signal detection unit 44 may be configured by a hardware resource such as an analog or digital circuit or may be configured by embedded software. The reception signal detection unit 44 may be provided for each reception signal, or one reception signal detection unit 44 may be provided with respect to plural reception signals.

In the present embodiment, as an example, the switching element 41 is off in an initial state, such as when the electronic cassette 12 is turned on. In a case in which the control unit 106 has detected the start of the application of the radiation, the switching element 41 switches on in accordance with the control signal, and the high-level transmission signal Fg is transmitted. In contrast, in a case in which the control unit 106 has not detected the start of the application of the radiation, the switching element 41 switches off in accordance with the control signal, and the low-level transmission signal Fg is transmitted.

In a case in which the control unit 106 has determined that noise is not occurring, the switching element 41 switches on in accordance with the control signal, and the high-level transmission signal Fg is transmitted. In a case in which the control unit 106 has determined that noise is occurring, the switching element 41 switches off in accordance with the control signal, and the low-level transmission signal Fg is transmitted.

In this way, in the present embodiment, the signals communicated between the radiographic imaging devices 14 are binary signals, and 1-bit signals are communicated at a time.

Figure 11:
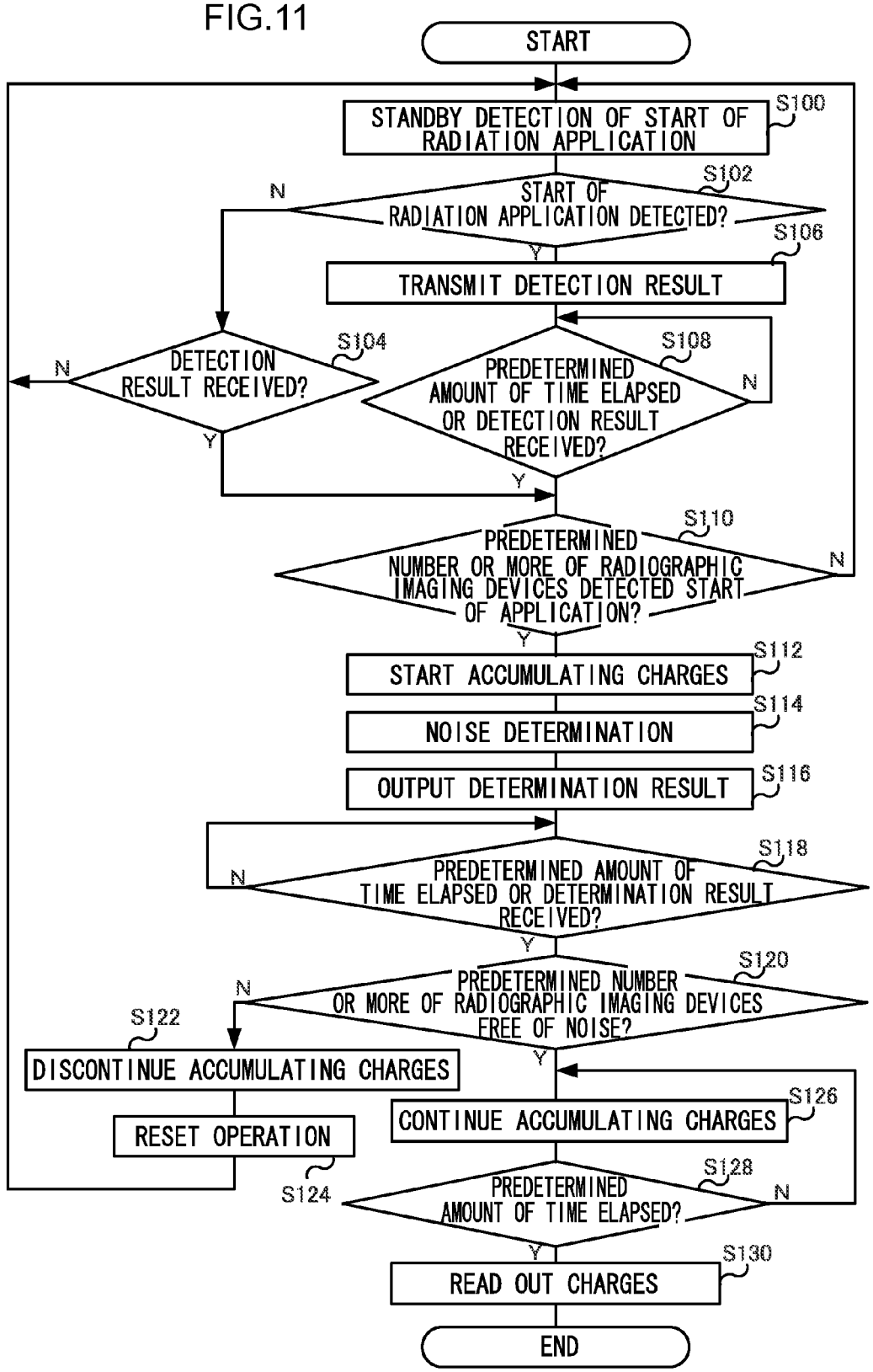
FIG. 11 is a flowchart of an exemplary flow of imaging operations when imaging a radiographic image pertaining to the first embodiment.

Next, details of a flow of imaging operations of a radiographic image with the electronic cassette 12 of the present embodiment will be described. FIG. 11 is a flowchart of an exemplary flow of imaging operations of a radiographic image.

Each of the radiographic imaging devices 14 of the electronic cassette 12 images a radiographic image by detecting the start of the application of the radiation, accumulating charges in the pixels 100 of the radiation detector 26, and outputting a radiographic image based on image data corresponding to the accumulated charges.

In the present embodiment, when radiographic imaging is performed, the radiographic imaging devices 14 are notified of a transition to an imaging mode. When the radiographic imaging devices 14 transitions to the imaging mode, the imaging operations illustrated in FIG. 11 start.

Figure 12:
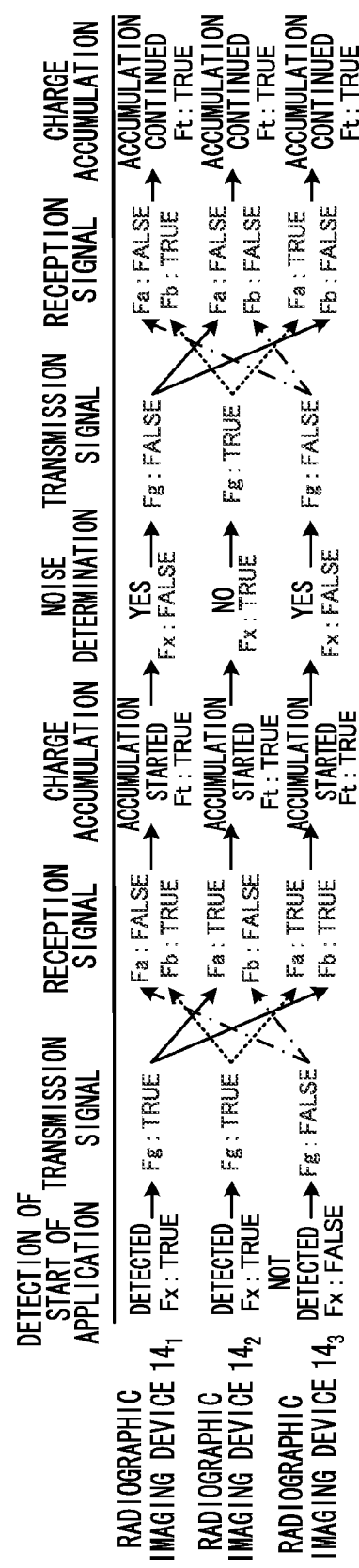
FIG. 12 is an explanatory drawing for describing a specific example of signals and flags in each of the radiographic imaging devices pertaining to the first embodiment.

Below, the case of the specific example illustrated in FIG. 12 will be described. As illustrated in FIG. 12, the radiographic imaging device $14_1$ detects the start of the application of the radiation and determines that noise is occurring. The radiographic imaging device $14_2$ detects the start of the application of the radiation and determines that noise is not occurring. The radiographic imaging device $14_3$ does not detect the start of the application of the radiation and determines that noise is occurring.

In step S100, the radiographic imaging device 14 transitions to a standby state for detecting the radiation. In the next step S102, the control unit 106 judges whether or not the start of the application of the radiation has been detected. In the present embodiment, the flag Fx becomes a high level (TRUE) in a case in which the control unit 106 has detected the start of the application of the radiation, and the flag Fx remains at a low level (FALSE) in a case in which the control unit 106 has not detected the start of the application of the radiation. In the radiographic imaging device 14, at the time when the control unit 106 has detected the start of the application of the radiation, the control unit 106 cannot distinguish between charges generated by noise and charges generated by the application of the radiation and, therefore, cannot determine whether or not noise is occurring. For that reason, the control unit 106 considers that the start of the application of the radiation has been detected even if the detection is a misdetection caused by noise.

In a case in which the control unit 106 has not detected the start of the application of the radiation, the processing proceeds to step S104 where the control unit 106 judges whether or not a predetermined amount of time has elapsed or whether or not it has received a detection result from another radiographic imaging device 14.

In the radiographic imaging system 10, two cases may be given as cases in which the control unit 106 of the radiographic imaging device 14 does not detect that the application of the radiation has been started. The first is a case in which the radiation is actually not applied from the radiographic application device 16, and in this case the control units 106 of all the radiographic imaging devices 14 do not detect that the application of the radiation has been started. The second is a case in which, in the local radiographic imaging device 14, the amount of radiation applied is small and the control unit 106 does not detect that the application of the radiation has been started, while in the other radiographic imaging devices 14, the control units 106 have detected that the application of the radiation has been started. In the second case, the reception unit 34 receives the detection result signals that have been transmitted by the processing of later-described step S106 executed by the other radiographic imaging devices 14.

Thus, because there are above two cases, in step S104 the control unit 106 judges whether or not the reception unit 34 has received a detection result signal. In a case in which the reception unit 34 has not received a detection result signal, the control unit 106 returns to step S100 and repeats the processing. In a case in which the reception unit 34 has received a detection result signal, the processing proceeds to step S110.

When the radiation is applied from the radiation application device 16, the applied radiation is absorbed by the scintillator of the radiation detector 26 and is converted into visible light. The radiation may be applied from either the front side or the back side of the radiation detector 26. The visible light into which the radiation has been converted by the scintillator is applied to the sensor portions 103 of the pixels 100.

When the light is applied to the sensor portions 103, charges are generated inside the sensor portions 103. The generated charges are collected by the lower electrodes 81.

In the radiographic imaging pixels 100A, the drain electrode 83 and the source electrode 79 are not shorted, and the charges collected by the lower electrodes 81 are accumulated. However, in the radiation detection pixels 100B, the drain electrode 83 and the source electrode 79 are shorted, and the charges collected by the lower electrodes 81 flow out to the signal lines 73.

In the electronic cassette 12, as described above, the electrical signals that have been output from the radiation detection pixels 100B are detected by the amplifier circuits of the signal detection circuit 105. The control unit 106 compares the detected electrical signals with a detection threshold value determined in advance and detects the start of the application of the radiation based on whether or not the electrical signals are equal to or greater than the threshold value. When the control unit 106 detects the start of the application of the radiation, the control unit 106 proceeds to step S106 where, on the basis of the flag Fx, a transmission signal Fg (Fx=Fg), which is a detection result signal indicating that the control unit 106 has detected the start of the application, is transmitted to the other radiographic imaging devices 14.

In the specific example illustrated in FIG. 12, the radiographic imaging device 14₁ transmits a high-level (TRUE) transmission signal Fg, the radiographic imaging device 14₂ receives a high-level reception signal Fa, and the radiographic imaging device 14₃ receives a high-level reception signal Fb. The radiographic imaging device 14₂ transmits a high-level (TRUE) transmission signal Fg, the radiographic imaging device 14₁ receives a high-level reception signal Fb, and the radiographic imaging device 14₃ receives a high-level reception signal Fa.

Although the radiographic imaging devices 14₁ and 14₂ both detect the start of the application of the radiation and output a high-level transmission signal Fg, the timings when they output the signals may not be simultaneous. In a case in which the amount of radiation applied to the radiation detectors 26 of the radiographic imaging devices 14₁ and 14₂ are different, there are cases in which the timings when the control units 106 detect the start of the application are different.

Since the radiographic imaging device 14₃ does not detect the start of the application of the radiation, a low-level (FALSE) signal that is an initial state is transmitted. The radiographic imaging device 14₁ receives a low-level reception signal Fa, and the radiographic imaging device 14₂ receives a low-level reception signal Fb.

In the next step S108, the control unit 106 judges whether or not a predetermined amount of time has elapsed or whether or not a detection result signal (in the present embodiment, a high-level signal) has been received. For example, there are cases in which, while the start of the application of the radiation is detected in the local device, the start of the application of the radiation has not been detected in any of the other radiographic imaging devices 14. In this case, the local device does not receive a detection result signal (a high-level signal) and, therefore, in the present embodiment, the control unit 106 judges whether or not a predetermined amount of time has elapsed, such as, for example, whether or not a predetermined amount of time has elapsed since the start of the application of the radiation is detected in the local device.

The predetermined amount of time may be determined in advance in accordance with the type of imaging and the characteristics of the radiographic imaging device 14. From the standpoint of ensuring real time imaging, it is preferable that the predetermined amount of time is short. The predetermined amount of time may be determined in consideration of a synchronous tolerable time difference (details described later). For example, about 1 msec is preferable and 1 msec or less is more preferable.

In step S108, in a case in which the predetermined amount of time has not elapsed or the reception unit 34 has not received a high-level signal as a detection result signal, the processing returns to step S108 and the radiographic imaging device 14 stands by. In a case in which the predetermined amount of time has elapsed or the reception unit 34 has received a high-level signal as a detection result signal, the processing proceeds to step S110.

In step S110, the control unit 106 judges whether or not a predetermined number or more of the radiographic imaging devices 14, including the local device, have detected the start of the application. In the present embodiment, as a specific example, the control unit 106 judges whether or not one or more of the radiographic imaging devices 14 have detected the start of the application. Consequently, the control unit 106 judges that the predetermined number or more of the radiographic imaging devices 14 have detected the start of the application of the radiation if one or more of the flag Fx and the reception signals Fa and Fb is a high level. The predetermined number is not limited to one as in the present embodiment. The predetermined number may also be determined in accordance with the type of imaging and the size of the radiation detector 26 (the size of the imaging plane).

In a case in which the predetermined number or more of the radiographic imaging devices 14 have not detected the start of the application of the radiation, the processing returns to step S100 and repeats the processing. In a case in which the predetermined number or more of the radiographic imaging devices 14 have detected the start of the application of the radiation, the processing proceeds to step S112.

In step S112, each of the radiographic imaging devices 14 starts accumulating the charges generated in the pixels 100 in accordance with the applied radiation. In the present embodiment, in a case in which the radiographic imaging device 14 is accumulating charges, the flag Ft becomes a high level (TRUE), and in a case in which the radiographic imaging device 14 is not accumulating charges, the flag Ft becomes a low level (FALSE).

In this way, since each of the radiographic imaging devices 14 starts accumulating the charges, the times when the radiographic imaging devices 14 start accumulating the charges are synchronous, and time differences between when the devices start the accumulation (synchronous tolerable time difference) are kept within about 1 msec. In a case in which the times when all the radiographic imaging devices 14 start accumulating the charges are not synchronous, there are cases in which radiation loss occurs and the percentage of the amount of radiation that does not contribute to the radiographic image increases, which may no longer be ignored or may cause artifacts in the radiographic image. However, in the electronic cassette 12 of the present embodiment, the times when the radiographic imaging devices 14 start accumulating the charges are synchronized, and radiation loss can be reduced. The synchronous tolerable time difference is not limited to 1 msec. The synchronous tolerable time difference is determined by tolerable artifacts, the imaging region of the subject 18, radiation application conditions or the like.

In the radiographic imaging pixels 100A of the radiation detector 26, the TFT switches 74 remain off, so the charges remain accumulated. However, in the radiation detection pixels 100B, since the TFT switches 74 are shorted, even during the charge accumulation period (when the TFT switches 74 are off), the charges are output to the signal detection circuit 105. At a predetermined timing the control unit 106 reads out, as electrical signals from the signal detection circuit 105, the information of the charges that have been output from the radiation detection pixels 100B.

In the next step S114, the control unit 106 of each of the radiographic imaging devices 14 judges whether or not noise has occurred. In a case in which noise is occurring, that is, in a case in which the detection of the start of the application of the radiation was a misdetection, it is necessary for the radiographic imaging device 14 to return as quickly as possible to the standby state to detect the start of the application of the radiation. In the case of a misdetection, during the period from the start of the accumulation of the charges to until the radiographic imaging device 14 returns again to the radiation application start detection standby state after detecting the start of the application of the radiation, the radiographic imaging device 14 becomes insensitive (cannot detect) the radiation. Therefore, in order to appropriately judge the start of the application, it is preferable for the amount of time until the radiographic imaging device 14 returns to the detection standby state to be as short as possible, such as, for example, 300 msec or less.

As described above, the control unit 106 continues detecting the electrical signals output from the radiation detection pixels 100B and judges whether or not noise has occurred based on whether or not the temporal changes in the electrical signals in the predetermined detection period have the noise characteristic.

In the present embodiment, in a case in which the control unit 106 has determined that noise is not occurring, the flag Fx becomes a high level (TRUE), and in a case in which the control unit 106 has determined that noise is occurring, the flag Fx becomes a low level (FALSE).

In the next step S116, on the basis of the flag Fx, a transmission signal Fg (Fx=Fg) that is a noise determination result signal is transmitted to the other radiographic imaging devices 14.

In the next step S118, the control unit 106 judges whether or not a predetermined amount of time has elapsed or whether or not a determination result signal (in the present embodiment, a high-level signal) has been received. In this step, similarly to step S108 described above, the control unit 106 judges whether or not a predetermined amount of time has elapsed after making the noise occurrence determination in the local device, for example.

In step S118, in a case in which the predetermined amount of time has not elapsed or the reception unit 34 has not received a high-level signal as a determination result signal, the local device stands by. In a case in which the predetermined amount of time has elapsed or the reception unit 34 has received a high-level signal as a determination result signal, the processing proceeds to step S120.

In step S120, the control unit 106 judges whether or not a predetermined number or more of the radiographic imaging devices 14, including the local device, have determined that noise is not occurring. In the present embodiment, as a specific example, the control unit 106 judges whether or not one or more of the radiographic imaging devices 14 have determined that noise is not occurring. That is, the control unit 106 judges that the predetermined number or more of the radiographic imaging devices 106 have determined that noise is not occurring if one or more of the flag Fx and the reception signals Fa and Fb is a high level. The predetermined number is not limited to one as in the present embodiment. The predetermined number may be determined in accordance with the type of imaging and the desired image quality of the radiographic image.

Figure 13:
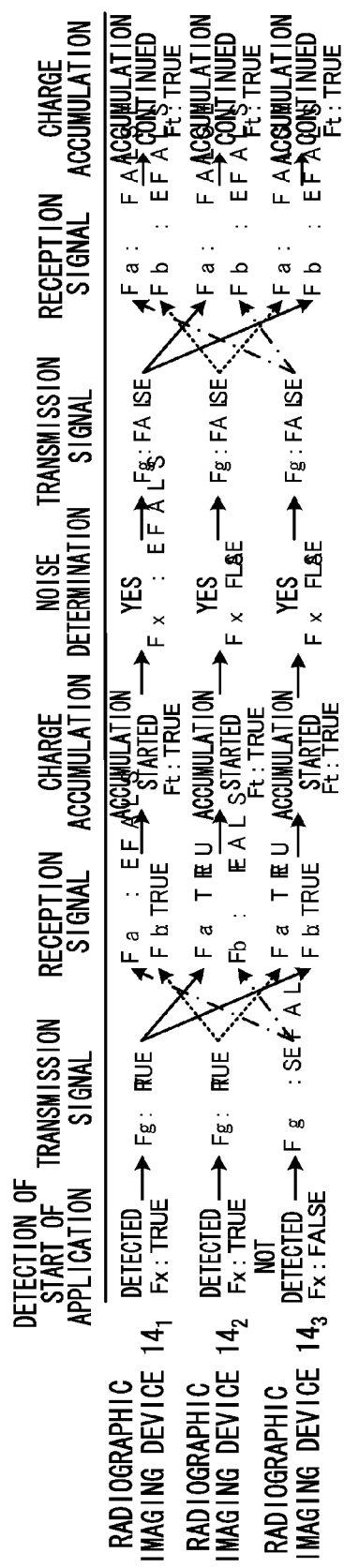
FIG. 13 is an explanatory drawing describing a specific example of signals and flags in a case in which it has been determined that noise is occurring in all of the radiographic imaging devices pertaining to the first embodiment.

In a case in which less than the predetermined number of the radiographic imaging devices 14 have determined that noise is not occurring (or in a case in which the predetermined number or more of the radiographic imaging devices 14 have determined that noise is occurring), the processing proceeds to step S122. In the present embodiment, as a specific example, the processing proceeds to step S122 in a case in which all of the radiographic imaging devices 14 have determined that noise is occurring. FIG. 13 illustrates a specific example of the signals and flags in a case in which all of the radiographic imaging devices 14 have determined that noise is occurring.

In step S122, the control unit 106 of each of the radiographic imaging devices 14 discontinues accumulating the charges in the pixels 100 of the radiation detector 26. In this case, the flag Ft becomes a low level (FALSE).

The user, such as a doctor, may be notified that noise has occurred. The method of notification is not particularly limited. For example, the notification may be displayed on the display of the console 20, or an audio notification or the like may be given.

In the next step S124, the control unit 106 performs a reset operation, which resets the charges accumulated in the pixels 100, and discards the electrical signals in order to eliminate misjudgment of the detection of the start of the application of the radiation resulting from the charges accumulated in the pixels 100. After the reset operation, the processing returns to step S100, again transitions to the radiation application start detection standby state, and repeats the processing. When the reset operation is performed, the period performing the reset operation becomes a radiation insensitive period (a non-detection period). In order to shorten this period, it is preferable that an operation for resetting the plural gate lines 101 be performed at the same time.

In step 120, in a case in which the predetermined number or more of the radiographic imaging devices 14 have determined that noise is not occurring, the processing proceeds to step S126 and the radiographic imaging devices 14 continue accumulating the charges in the pixels 100. In this case, the flag Ft remains at a high level (TRUE).

In the next step S128, the control unit 106 judges, on the basis of a timer not illustrated in the drawings, whether or not a predetermined amount of time has elapsed since the start of the application of the radiation has been detected. In a case in which the predetermined amount of time has not elapsed, the determination is negative, the processing returns to step S126 and repeats the subsequent processing.

In a case in which the predetermined amount of time has elapsed, the processing proceeds to S130 where the control unit 106 reads out the charges accumulated by the pixels 100 and then the processing ends. Specifically, the control unit 106 sequentially applies on-signals via the gate lines 101 to the gate electrodes 72 of the TFT switches 74. Due to the application of the on-signals, the TFT switches 74 of the pixels 100A are sequentially switched on, and electrical signals corresponding to the charge quantities accumulated in the pixels 100A are output to the signal lines 73.

Second Embodiment

In the first embodiment, a case has described in which if the predetermined number or more of the radiographic imaging devices 14 among all of the radiographic imaging devices 14 included in the electronic cassette 12 have detected the start of the application of the radiation, the control unit 106 starts accumulating the charges, and if the predetermined number or more of the radiographic imaging devices 14 among all of the radiographic imaging devices 14 have determined that noise is not occurring, the control unit 106 continues accumulating the charges. In the present embodiment, a case will be described in which, if a predetermined number or more of the radiographic imaging devices 14, among the radiographic imaging devices 14 that have detected the start of the application of the radiation, have determined that noise is not occurring, the control unit 106 continues accumulating the charges.

The configurations of the radiographic imaging system 10, the electronic cassette 12, and the radiographic imaging devices 14 are similar to those in the first embodiment, so description thereof will be omitted.

In each of the radiographic imaging devices 14 of the present embodiment, since the imaging operations of a radiographic image are partially different from those of the first embodiment, only the operations that are different will be described in detail.

Figure 14:
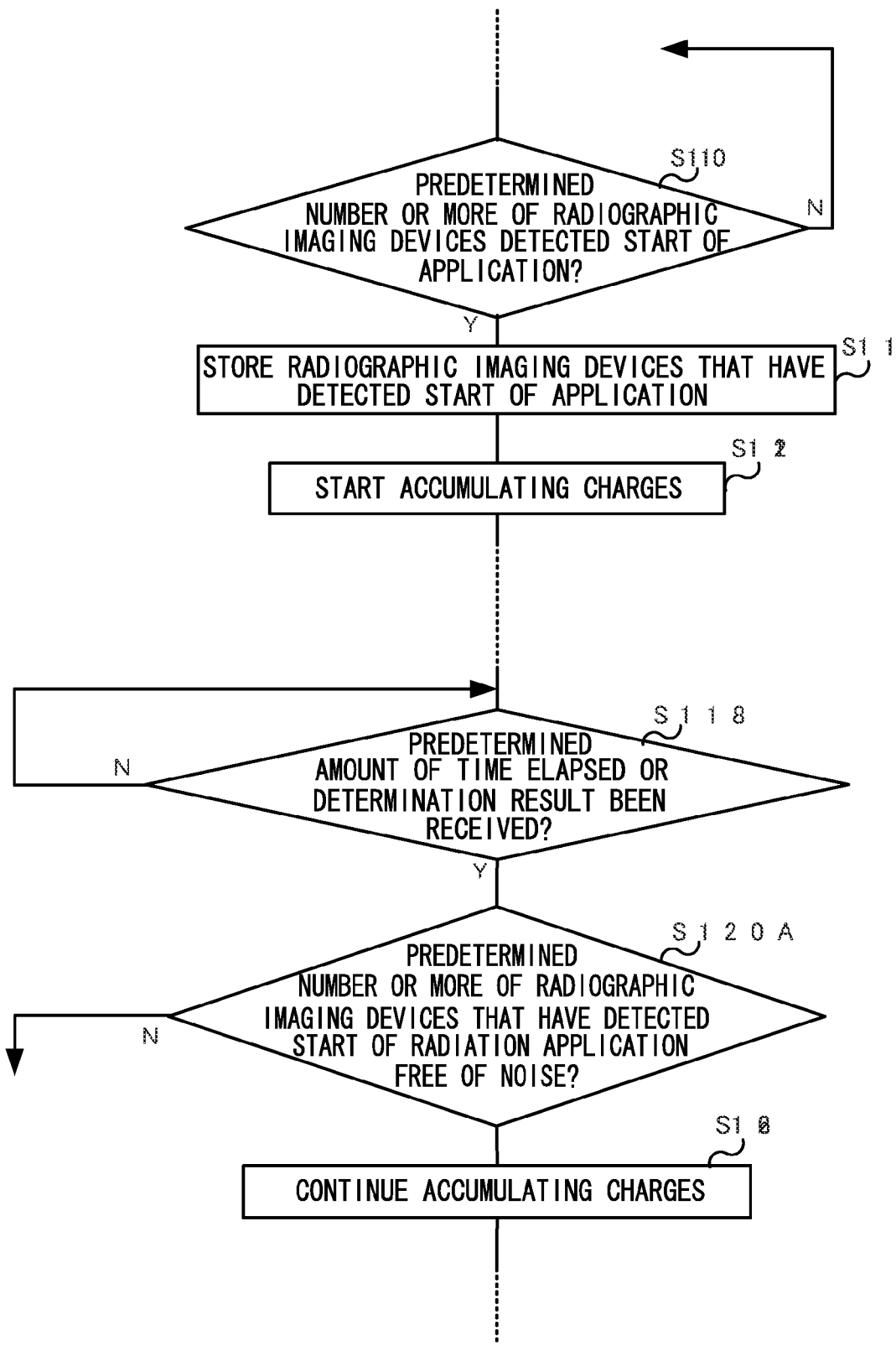
FIG. 14 is a flowchart of an exemplary flow of imaging operations of a radiographic image pertaining to a second embodiment.

FIG. 14 is a flowchart of an exemplary flow of imaging operations of a radiographic image. In FIG. 14, some of the operations that are similar to the imaging operations of the first embodiment (see FIG. 11) are not illustrated.

In the imaging operations executed by the control unit 106 of each of the radiographic imaging devices 14, as illustrated in FIG. 14, step S111 is added between step S110 and step S112.

In step S110, as described above, the control unit 106 judges whether or not the predetermined number or more of the radiographic imaging devices 14, including the local device, have detected the start of the application of the radiation. In a case in which the predetermined number or more of the radiographic imaging devices 14 have detected the start of the application of the radiation, the processing proceeds to step S111.

In step S111, the control unit 106 stores information identifying which radiographic imaging devices 14, including the local device, have detected the start of the application of the radiation, and thereafter proceeds to step S112. For example, the information may be stored in a storage unit located in the control unit 106. The information identifying the radiographic imaging devices 14 is not particularly limited and, for example, may be numbers (IDs or the like) associated with the radiographic imaging devices 14 or may be information corresponding to the transmission terminals 33 and the reception terminals 35 (35a or 35b).

Moreover, in the imaging operations in the radiographic imaging devices 14 of the present embodiment, as illustrated in FIG. 14, step S120A is provided instead of step S120 between step S118 and step S126.

In step S118, as described above, the control unit 106 judges whether or not a predetermined amount of time has elapsed or whether or not the reception unit 34 has received a high-level signal as a determination result signal. In a case in which the predetermined amount of time has elapsed or the reception unit 34 has received a high-level signal as a determination result signal, the processing proceeds to step S120A.

In step S120A, the control unit 106 judges whether or not a predetermined number or more of the radiographic imaging devices 14, among the radiographic imaging devices 14 that have detected the start of the application of the radiation, have determined that noise is not occurring, the processing proceeds to step S126 or step S122 depending on the judgment. In the present embodiment, as a specific example, the control unit 106 judges whether or not one or more of the radiographic imaging devices 14 among the radiographic imaging devices 14 stored by step S111 as having detected the start of the application of the radiation have determined that noise is not occurring.

That is, in the present embodiment, the control unit 106 judges whether or not the number of radiographic imaging devices 14 in which the start of the application of the radiation in step S102 has been appropriately performed (not a misdetection) is equal to or greater than the predetermined number (one). If the number is equal to or greater than one, the processing proceeds to step S126 where the radiographic imaging devices 14 continue accumulation of the charges in the pixels 100.

Third Embodiment

In the first embodiment and the second embodiment, cases have been described in which the radiographic imaging devices 14 are connected in parallel to one another. In the present embodiment, a case will be described in which the radiographic imaging devices 14 are connected in series to one another.

The configurations of the radiographic imaging system 10 and the electronic cassette 12 are similar to those in the first embodiment, so description thereof will be omitted. In the present embodiment, since the connection of the radiographic imaging devices 14 is different, the configuration relating to the connection will be specifically described.

Figure 15:
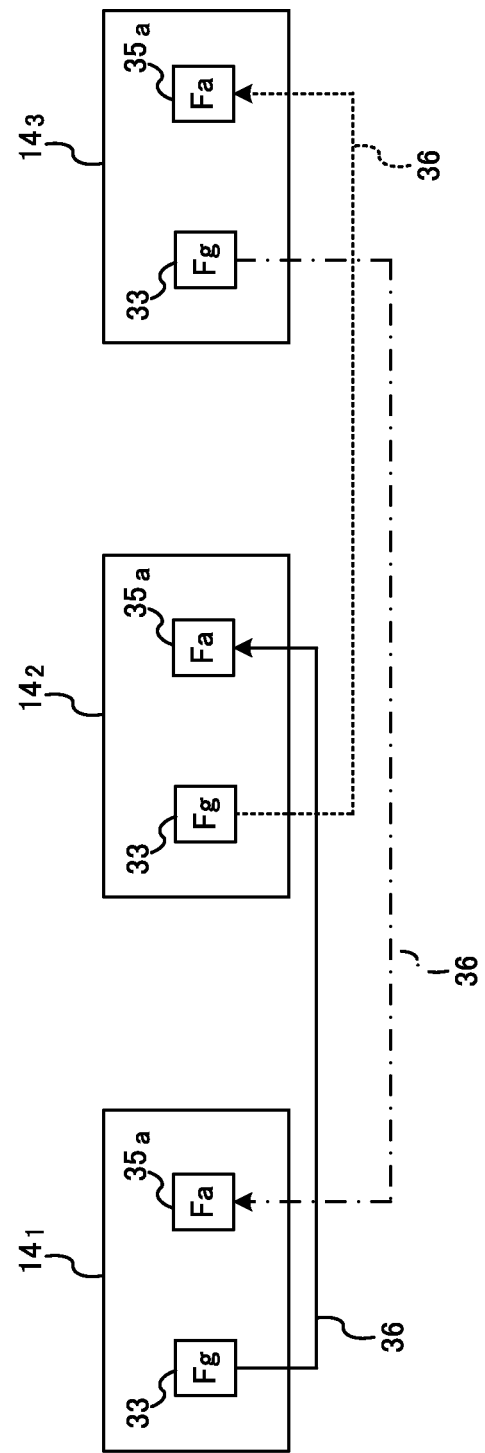
FIG. 15 is an explanatory drawing for describing an example of a connection relationship between three radiographic imaging devices pertaining to a third embodiment.

FIG. 15 is an explanatory drawing for describing an example of a connection relationship between radiographic imaging devices $14_1$ to $14_3$.

As illustrated in FIG. 15, in the present embodiment, three radiographic imaging devices 14 ($14_1$ to $14_3$) are electrically connected in series to one another by wires. Because the radiographic imaging devices 14 are connected to another one in series, they are each equipped with one reception terminal 35a regardless of the number of the radiographic imaging devices 14 included in the electronic cassette 12.

In the present embodiment, the transmission terminal 33 of the radiographic imaging device $14_1$ is connected by a signal wire 36 to the reception terminal 35a of the radiographic imaging device $14_2$. A transmission signal Fg transmitted from the transmission terminal 33 of the radiographic imaging device $14_1$ is received as a reception signal Fa by the reception terminal 35a of the radiographic imaging device $14_2$.

Similarly, the transmission terminal 33 of the radiographic imaging device $14_2$ is connected by a signal wire 36 to the reception terminal 35a of the radiographic imaging device $14_3$. A transmission signal Fg transmitted from the transmission terminal 33 of the radiographic imaging device $14_2$ is received as a reception signal Fa by the reception terminal 35a of the radiographic imaging device $14_3$. Further similarly, the transmission terminal 33 of the radiographic imaging device $14_3$ is connected by a signal wire 36 to the reception terminal 35a of the radiographic imaging device $14_1$. A transmission signal Fg transmitted from the transmission terminal 33 of the radiographic imaging device $14_3$ is received as a reception signal Fa by the reception terminal 35a of the radiographic imaging device $14_1$.

Next, imaging operations of a radiographic image in the radiographic imaging devices 14 of the present embodiment will be described.

In the present embodiment, the detection result signal and the determination result signal are binary (1-bit) signals as in the above embodiments. However, in contrast to the above embodiments, since the radiographic imaging devices 14 are connected in series to one another, the detection result and the determination result are circularly referenced. Therefore, the imaging operations are partially different from those of the above embodiments.

Figure 16:
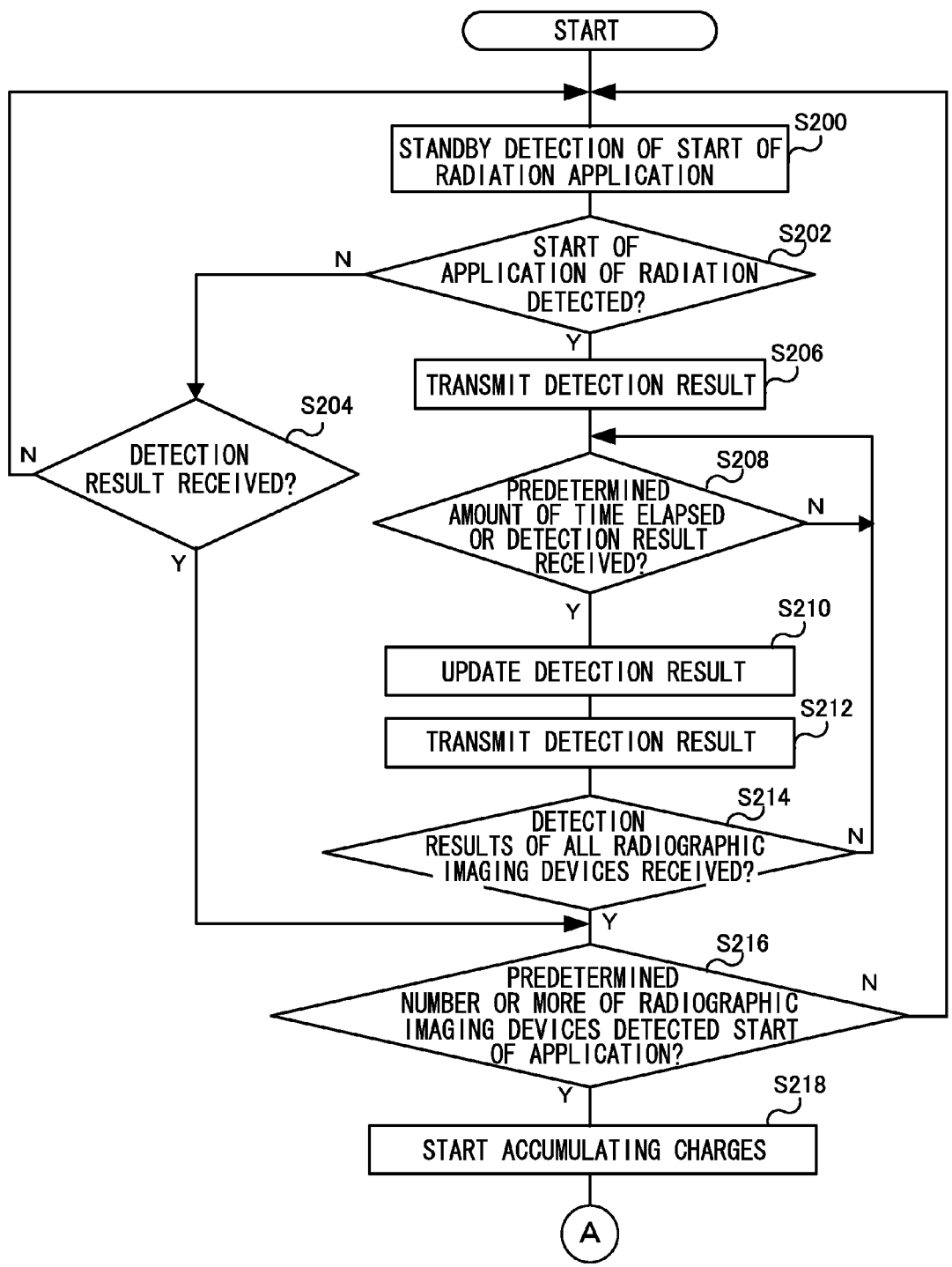
FIG. 16 is a flowchart of an exemplary flow of imaging operations of a radiographic image pertaining to the third embodiment.
Figure 17:
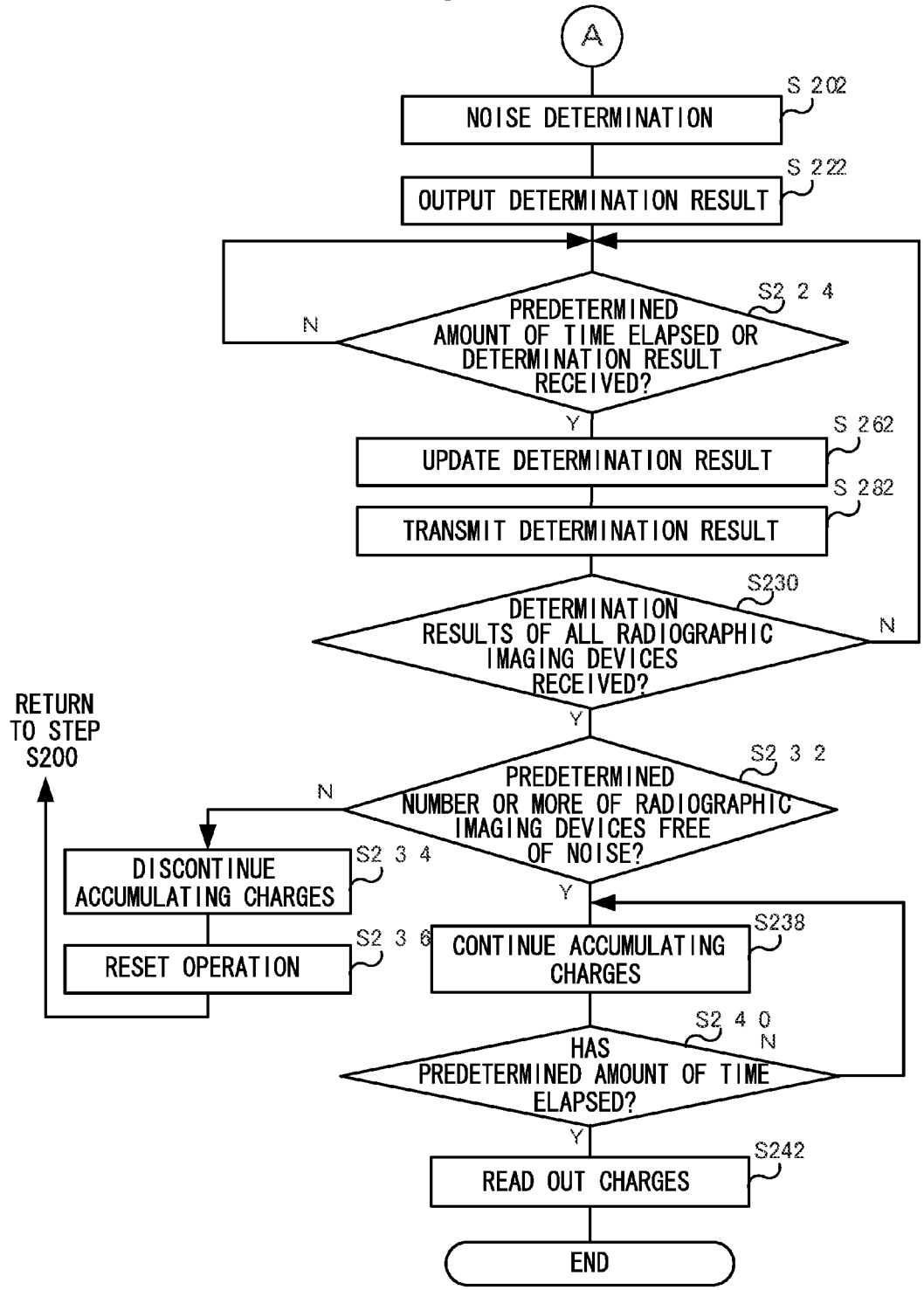
FIG. 17 is a flowchart of an exemplary flow of imaging operations of a radiographic image pertaining to the third embodiment.

FIG. 16 and FIG. 17 are flowcharts of an exemplary flow of imaging operations of a radiographic image. In the radiographic imaging devices 14 of the present embodiment, as in the first embodiment, the control unit 106 starts accumulating the charges in a case in which a predetermined number (=1) or more of the radiographic imaging devices 14 have detected the start of the application of the radiation. Furthermore, in the radiographic imaging devices 14 of the present embodiment, as in the first embodiment, the control unit 106 continues accumulating the charges in a case in which the predetermined number (=1) or more of the radiographic imaging devices 14 have determined that noise is not occurring.

Since the imaging operations in the radiographic imaging devices 14 of the present embodiment include operations similar to the imaging operations of the first embodiment (see FIG. 11), similar operations are indicated as such and detailed description thereof will be omitted.

The operations of steps S200 to S208 correspond to the operations of steps S100 to S108 of the first embodiment, respectively.

In step S200, the radiographic imaging device 14 transitions to a standby state for detecting the radiation. In the next step S202, the control unit 106 judges whether or not the start of the application of the radiation has been detected. In a case in which the control unit 106 has not detected the start of the application of the radiation, the processing proceeds to step S204 where the control unit 106 judges whether or not a predetermined amount of time has elapsed or whether or not a detection result has been received from another radiographic imaging device 14. In a case in which a detection result signal has not been received, the processing returns to step S200 and repeats the subsequent processing. In a case in which a detection result signal has been received, the processing proceeds to step S216.

In a case in which the control unit 106 detects the start of the application of the radiation, the processing proceeds to step S206 where, on the basis of the flag Fx, a transmission signal Fg (Fx=Fg), which is a detection result signal indicating that the start of the application has been detected, is transmitted to the other radiographic imaging devices 14.

Figure 18:
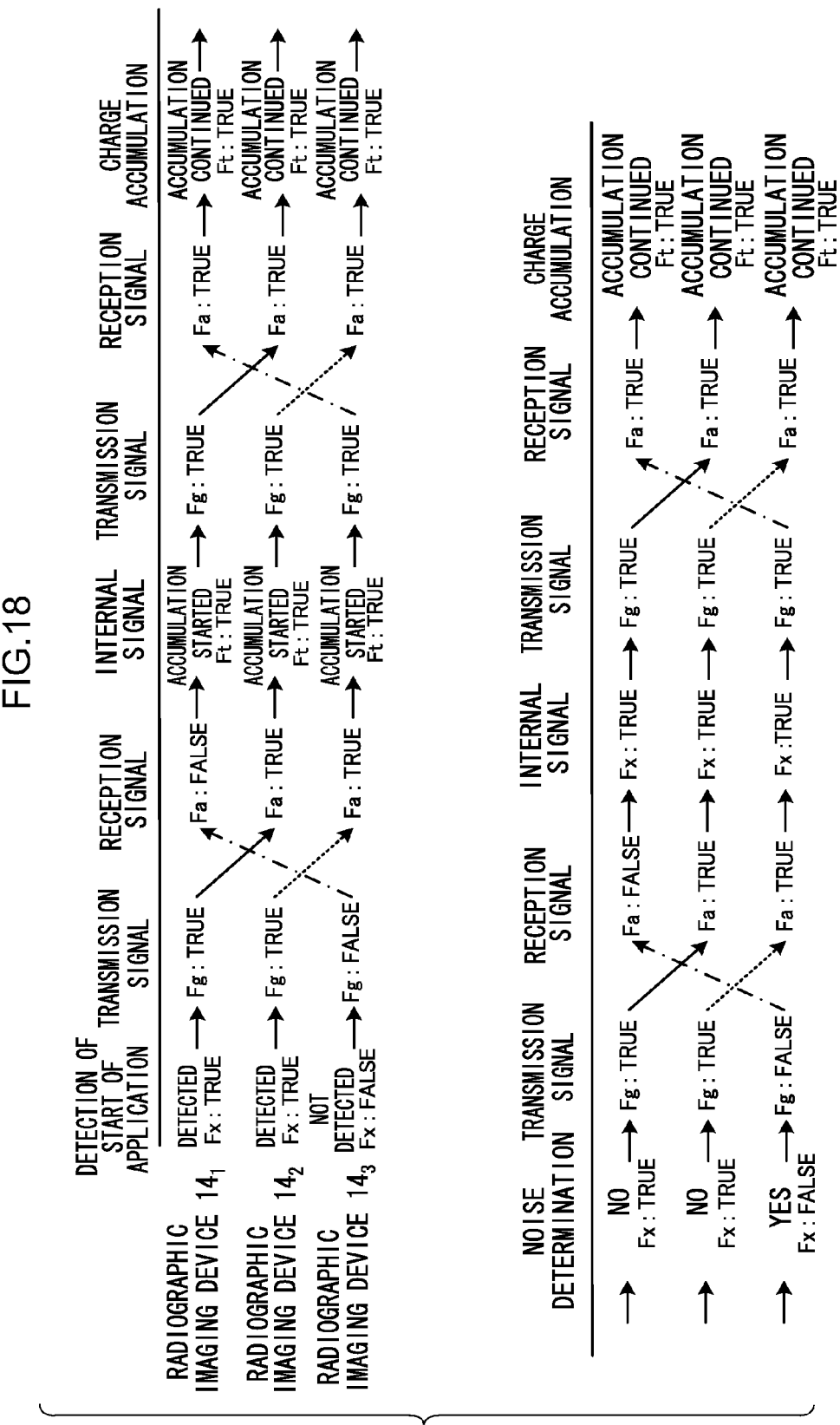
FIG. 18 is an explanatory drawing for describing a specific example of signals and flags in each of the radiographic imaging devices pertaining to the third embodiment.

In the specific example illustrated in FIG. 18, the radiographic imaging device $14_1$ transmits a high-level (TRUE) transmission signal Fg and the radiographic imaging device $14_2$ receives a high-level reception signal Fa. The radiographic imaging device $14_2$ transmits a high-level (TRUE) transmission signal Fg and the radiographic imaging device $14_3$ receives a high-level reception signal Fa. The radiographic imaging device $14_3$ transmits a low-level (FALSE) transmission signal Fg and the radiographic imaging device $14_1$ receives a low-level reception signal Fa. Since the radiographic imaging device $14_3$ does not detect the start of the application of the radiation, the radiographic imaging device $14_3$ transmits the low-level (FALSE) signal, which is an initial state and the radiographic imaging device $14_1$ receives the low-level reception signal Fa.

In the next step S208, the control unit 106 judges whether or not a predetermined amount of time has elapsed or whether or not a detection result signal has been received. In step S208, in a case in which the predetermined amount of time has not elapsed or the reception unit 34 has not received a detection result signal, the processing returns to step S208 and the local device stands by. In a case in which the predetermined amount of time has elapsed or the reception unit 34 has received a detection result signal, the processing proceeds to step S210.

In step S210, the control unit 106 updates the detection result (the flag Fx) based on the reception signal Fa and the flag Fx. In the present embodiment, the control unit 106 updates the detection result (the flag Fx) by performing an OR logic operation on the reception signal Fa and the flag Fx.

In the next step S212, similarly to step S206, the updated detection result is transmitted.

In the next step S214, the control unit 106 judges whether or not the detection results of all of the radiographic imaging devices 14 have been received. For example, the control unit 106 makes this judgment based on the number of receptions or whether or not a predetermined amount of time has elapsed. In the present embodiment, it may be judged that the detection results of all of the radiographic imaging devices 14 have been received in a case in which detection result signals have been received two times. The processing returns to step S208 and repeats the subsequent processing until the detection results of all of the radiographic imaging devices 14 have been received. In a case in which the detection results of all of the radiographic imaging devices 14 have been received, the processing proceeds to step S216.

Step S216 corresponds to step S110 of the first embodiment. In step S216, the control unit 106 judges whether or not a predetermined number or more of the radiographic imaging devices 14, including the local device, have detected the start of the application of the radiation. In the present embodiment, the detection result of the local device is also included in the last received reception signal Fa, and since the predetermined number is 1, the processing proceeds to step S218 if the reception signal Fa is a high level (TRUE). If the reception signal Fa is a low level (FALSE), the processing returns to step S208 and repeats the subsequent processing.

The operations of steps S218 to S224 correspond to the operations of steps S112 to S118 of the first embodiment, respectively.

In step S218, each of the radiographic imaging devices 14 starts accumulating the charges generated in the pixels 100 in accordance with the applied radiation. In the next step S220, the control unit 106 of each of the radiographic imaging devices 14 judges whether or not noise has occurred. In the next step S222, on the basis of the flag Fx, a transmission signal Fg (Fx=Fg) that is a noise determination result signal is transmitted to the other radiographic imaging devices 14.

In the next step S224, the control unit 106 judges whether or not a predetermined amount of time has elapsed or whether or not a detection result signal has been received.

In step S224, in a case in which the predetermined amount of time has not elapsed or the reception unit 34 has not received a determination result signal, the local device stands by. In a case in which the predetermined amount of time has elapsed or the reception unit 34 has received a determination result signal, the processing proceeds to step S226.

In step S226, similarly to step S210, the control unit 106 updates the determination result (the flag Fx) on the basis of the reception signal Fa and the flag Fx. In the present embodiment, the control unit 106 updates the detection result (the flag Fx) by performing an OR logic operation on the reception signal Fa and the flag Fx.

In the next step S228, similarly to step S212, the updated detection result is transmitted.

In the next step S230, similarly to step S214, the control unit 106 judges whether or not the determination results of all of the radiographic imaging devices 14 have been received. For example, the control unit 106 makes this judgment based on the number of receptions or whether or not a predetermined amount of time has elapsed. In the present embodiment, it may be judged that the determination results of all of the radiographic imaging devices 14 have been received in a case in which determination result signals have been received two times. The processing returns to step S224 and repeats the subsequent processing until the determination results of all of the radiographic imaging devices 14 have been received. In a case in which the determination results of all of the radiographic imaging devices 14 have been received, the processing proceeds to step S232.

Step S232 corresponds to step S120 of the first embodiment. In step S232, the control unit 106 judges whether or not a predetermined number or more of the radiographic imaging devices 14, including the local device, have detected that noise is occurring. In the present embodiment, the determination result of the local device is also included in the last received reception signal Fa, and since the predetermined number is 1, the processing proceeds to step S238 if the reception signal Fa is a high level (TRUE). If the reception signal Fa is a low level (FALSE), the processing proceeds to S234.

The subsequent steps S234 to S242 until ending the processing correspond to steps S122 to S130 of the first embodiment, respectively, so description thereof will be omitted.

Fourth Embodiment

In the above embodiments, cases have been described in which one radiographic imaging device 14 is directly connected to all of the other radiographic imaging devices 14 and directly transmits a transmission signal Fg to all of the other radiographic imaging devices 14. In contrast, in the present embodiment, a case will be described in which the radiographic imaging devices 14 disposed with a predetermined separation therebetween are not directly connected with each other, but are connected via another radiographic imaging device 14 disposed therebetween, and transmission signals (Fga, Fgb) corresponding to the transmission signal Fg are transmitted via the intervening radiographic imaging device 14.

Since the configurations of the radiographic imaging system 10 and the electronic cassette 12 are similar to those in the first embodiment, description thereof will be omitted.

In the present embodiment, since the configuration of the radiographic imaging devices 14 is different, the configuration of the radiographic imaging devices 14 will be specifically described.

Figure 19:
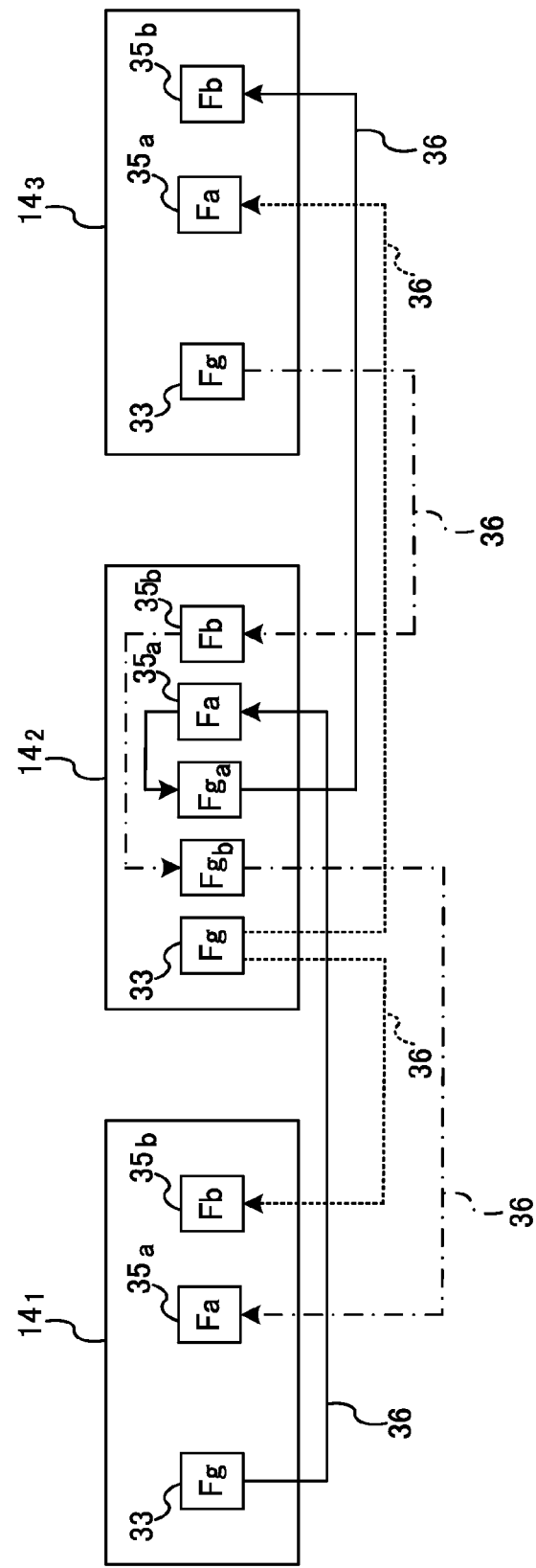
FIG. 19 is an explanatory drawing describing an example of a connection relationship between three radiographic imaging devices pertaining to a fourth embodiment.

FIG. 19 is an explanatory drawing describing an example of a connection relationship between the radiographic imaging devices $14_1$ to $14_3$ pertaining to the present embodiment.

As illustrated in FIG. 19, the radiographic imaging device $14_1$ is connected only to the radiographic imaging device $14_2$. Therefore, the transmission signal Fg transmitted by the radiographic imaging device $14_1$ is transmitted to the radiographic imaging device $14_3$ via the radiographic imaging device $14_2$.

The radiographic imaging device $14_2$ is connected to the radiographic imaging devices $14_1$ and $14_3$.

The radiographic imaging device $14_3$ is connected only to the radiographic imaging device $14_2$. Therefore, the transmission signal Fg transmitted by the radiographic imaging device $14_3$ is transmitted to the radiographic imaging device $14_1$ via the radiographic imaging device $14_2$.

Figure 20:
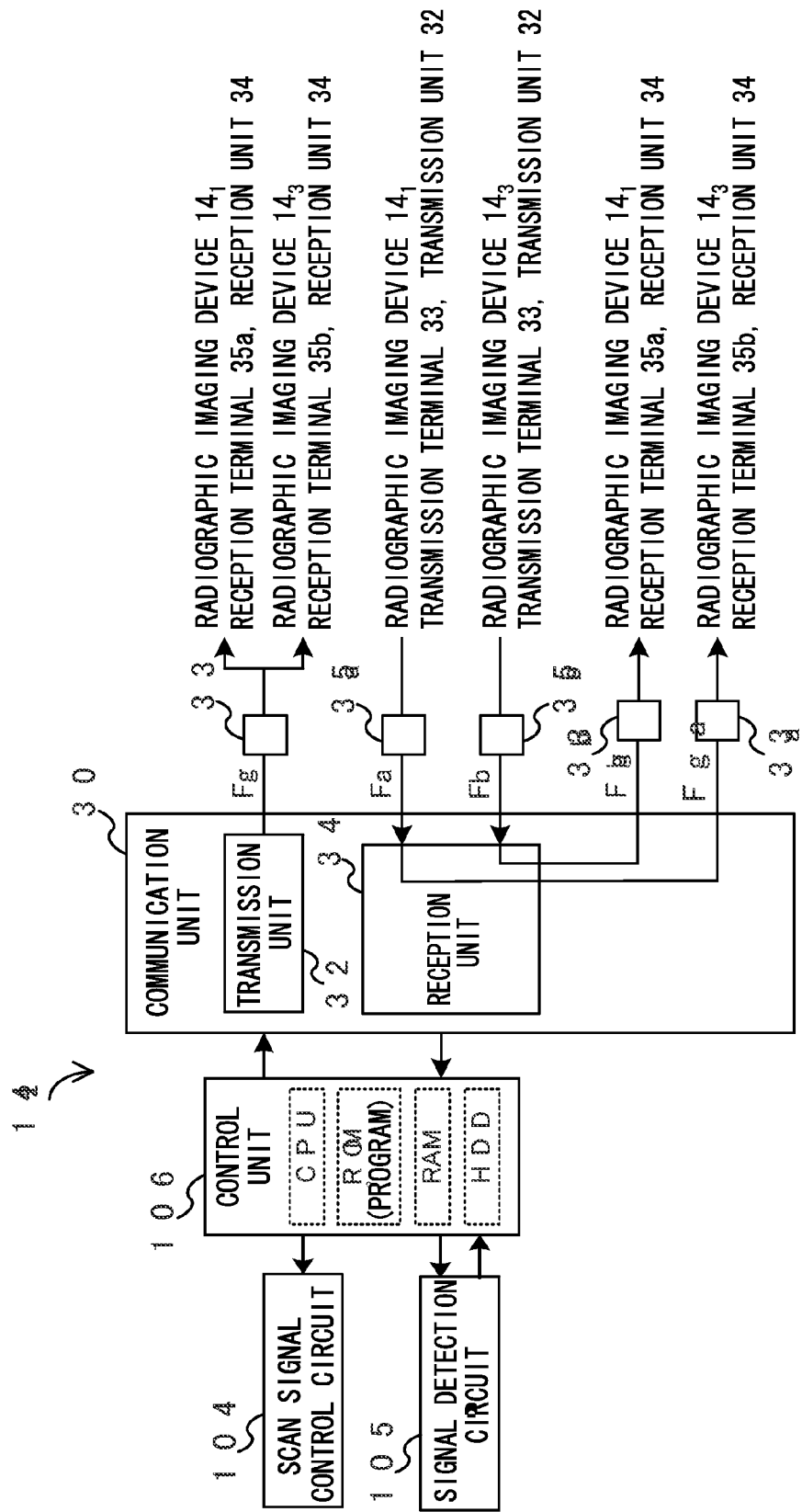
FIG. 20 is a schematic configuration diagram describing an exemplary configuration of a function of communicating a detection result and a determination result to other radiographic imaging devices to which the radiographic imaging device pertaining to the fourth embodiment is connected.

FIG. 20 is a schematic configuration diagram describing an exemplary configuration of a function of the radiographic imaging device $14_2$ for communicating a detection result and a determination result to the radiographic imaging devices $14_1$ and $14_3$ connected thereto.

As illustrated in FIG. 20, in the communication unit 30 of the radiographic imaging device $14_2$, the function of the reception unit 34 is different from that of the reception unit 34 (see FIG. 9) in the communication unit 30 of the radiographic imaging device 14 according to the first embodiment.

The transmission unit 32 and the reception unit 34 of the radiographic imaging device $14_2$ of the present embodiment have functions equivalent to those of the radiographic imaging device $14_2$ of the first embodiment. Therefore, the radiographic imaging device $14_2$ of the present embodiment is able to perform imaging operations (see FIG. 11) as well as the radiographic imaging device $14_2$ of the first embodiment.

In addition to the above function, the reception unit 34 of the radiographic imaging device $14_2$ of the present embodiment has a function of directly transmitting received reception signals Fa and Fb to another radiographic imaging device 14.

A reception signal Fa received by the reception unit 34 of the radiographic imaging device $14_2$ via the reception terminal 35a from the radiographic imaging device $14_1$ is transmitted to the radiographic imaging device $14_3$ as a transmission signal Fga via the transmission terminal 33a. The transmission signal Fga is received by the reception terminal 35b of the radiographic imaging device $14_3$ as a reception signal Fb.

In the radiographic imaging device $14_1$, a transmission signal Fgb corresponding to a transmission signal Fg transmitted by the radiographic imaging device $14_3$ is received by the reception terminal 35a, and a transmission signal Fg transmitted by the radiographic imaging device $14_2$ is received by the reception terminal 35b. Therefore, the radiographic imaging device $14_1$ may perform imaging operations similar to the radiographic imaging device $14_1$ of the first embodiment.

A reception signal Fb received by the reception unit 34 of the radiographic imaging device $14_2$ via the reception terminal 35b from the radiographic imaging device $14_3$ is transmitted to the radiographic imaging device $14_1$ as a transmission signal Fgb via the transmission terminal 33b. The transmission signal Fgb is received by the reception terminal 35a of the radiographic imaging device $14_1$ as a reception signal Fa.

In the radiographic imaging device $14_3$, a transmission signal Fg transmitted by the radiographic imaging device $14_2$ is received by the reception terminal 35a, and a transmission signal Fga corresponding to the transmission signal Fg transmitted by the radiographic imaging device $14_1$ is received by the reception terminal 35b. Therefore, the radiographic imaging device $14_3$ may perform imaging operations similar to the radiographic imaging device $14_3$ of the first embodiment.

Figure 21:
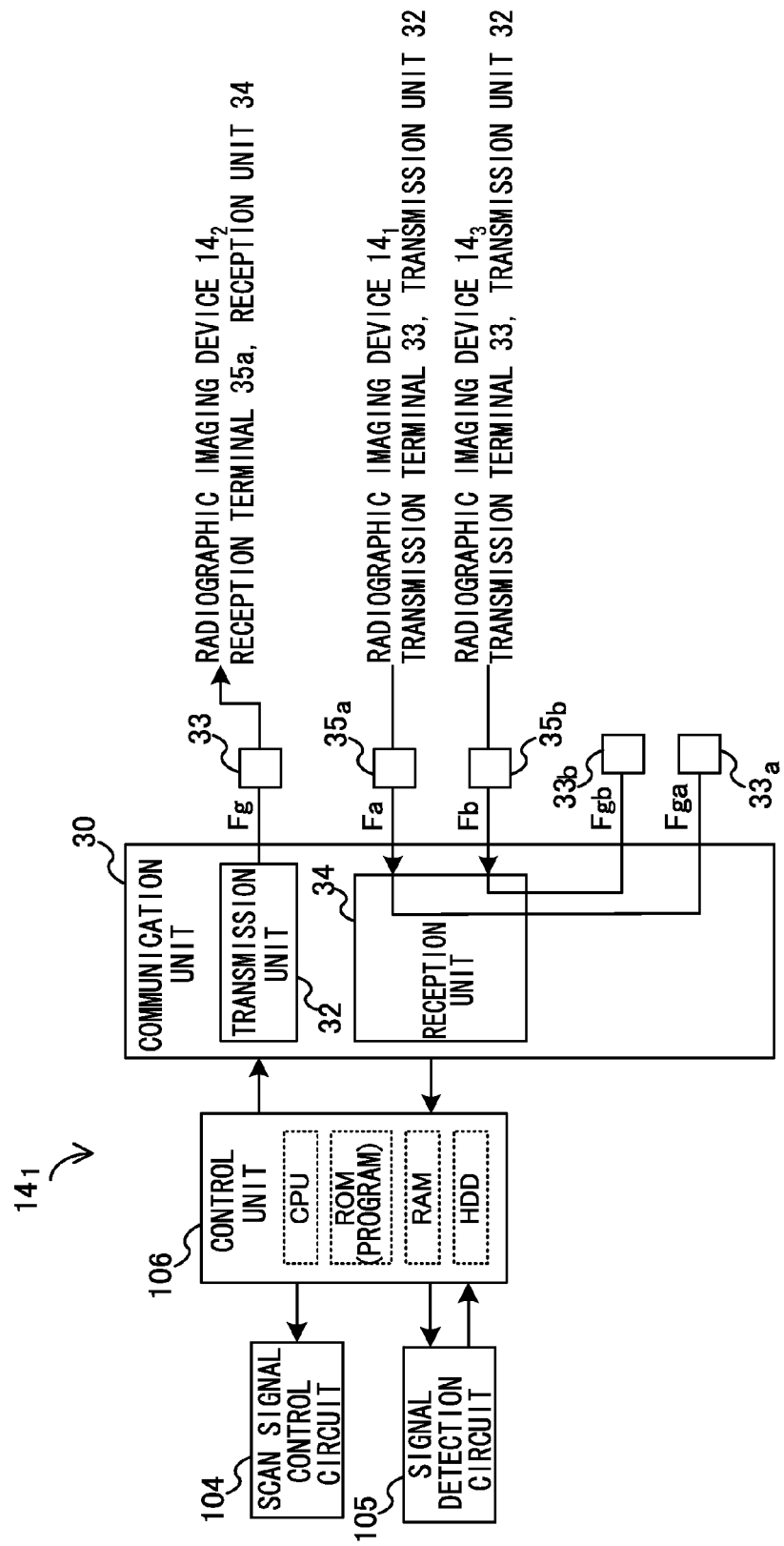
FIG. 21 is a schematic configuration diagram describing an exemplary configuration of a function of communicating a detection result and a determination result to other radiographic imaging devices to which the radiographic imaging device, which is different from that illustrated in FIG. 20, is connected.

The configurations of the radiographic imaging device $14_1$ and the radiographic imaging device $14_3$ of the present embodiment may be made similar to that of the radiographic imaging device $14_2$. A specific example of such a case will be described using the radiographic imaging device $14_1$. FIG. 21 is a schematic configuration diagram describing an exemplary configuration of a communication function of the radiographic imaging device $14_1$ in this case, for communicating detection results and determination results with the radiographic imaging devices $14_2$ and $14_3$ connected thereto.

As illustrated in FIG. 21, since only the radiographic imaging device $14_2$ is connected to the transmission terminal 33 of the radiographic imaging device $14_1$, the transmission unit 32 transmits a transmission signal Fg only to the radiographic imaging device $14_2$ via the transmission terminal 33.

Via the reception unit 34, the reception terminal 35a is connected to the transmission terminal 33a, and the reception terminal 35b is connected to the transmission terminal 33b. However, since no transmission destination is connected to either of the transmission terminal 33a or 33b, transmission signals Fga and Fgb, corresponding to reception signals Fa and Fb, are not transmitted from the radiographic imaging device $14_1$.

Thus, the radiographic imaging device $14_1$ and $14_3$ of the present embodiment may perform imaging operations similar to the radiographic imaging device 14 of the first embodiment.

In this way, by configuring all of the radiographic imaging devices 14 ($14_1$ to $14_3$) in the same configuration, the type of the radiographic imaging device 14 to be manufactured may be unified, making the manufacturing easy. Further, since the radiographic imaging devices 14 only need to be connected as described above, there is no need to consider the arranging positions of the radiographic imaging devices 14.

Figure 22:
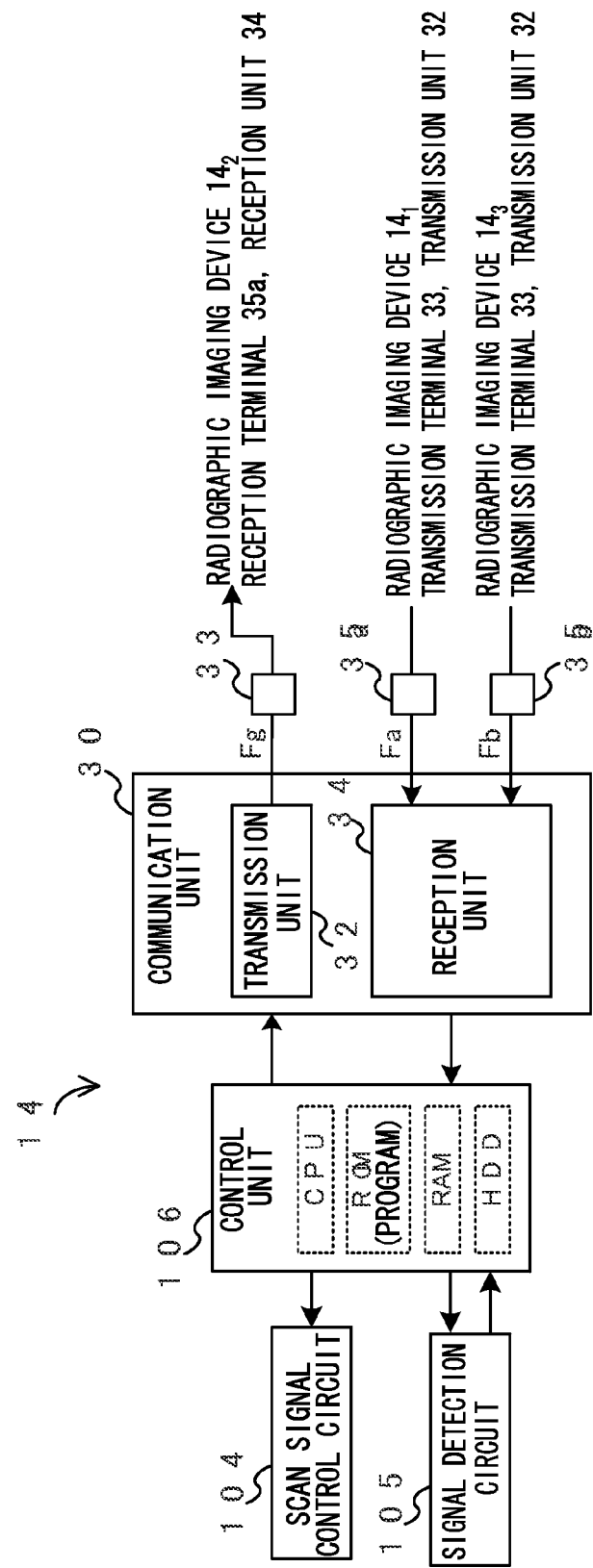
FIG. 22 is a schematic configuration diagram describing another exemplary configuration of a function of communicating a detection result and a determination result to other radiographic imaging devices to which the radiographic imaging device, which is different from that illustrated in FIG. 20, is connected.

Alternatively, the configurations of the radiographic imaging devices $14_1$ and $14_3$ of the present embodiment may be made similar to that of the radiographic imaging device 14 (see FIG. 9) of the first embodiment. FIG. 22 is a schematic configuration diagram describing an exemplary configuration of a communication function of the radiographic imaging device $14_1$ in this case, for communicating detection results and determination results with the radiographic imaging devices $14_2$ and $14_3$ connected thereto.

As illustrated in FIG. 22, in the communication unit 30 of the radiographic imaging device $14_1$ of the present embodiment, only the radiographic imaging device $14_2$ is connected to the transmission terminal 33, and the configuration is similar to the communication unit 30 of the first embodiment except that the transmission unit 32 transmits a transmission signal Fg only to the radiographic imaging device $14_2$ via the transmission terminal 33.

Thus, the radiographic imaging device $14_1$ and $14_3$ of the present embodiment may perform imaging operations similar to the radiographic imaging device 14 of the first embodiment.

In this way, by configuring the radiographic imaging devices $14_1$ and $14_3$ in the same configuration as the radiographic imaging device 14 of the first embodiment, more simple configuration may be adopted than that of the radiographic imaging devices $14_2$ of the present embodiment, in respect that the transmission terminal 33a and 33b are omitted.

While the present embodiment has been described related to a case in which three radiographic imaging devices 14 are used, in cases in which there are three or more radiographic imaging devices 14, two radiographic imaging devices 14 disposed with a predetermined separation (e.g., a separation corresponding to a length of a predetermined number of radiographic imaging devices 14) may not be directly connected with each other, and may be connected via other radiographic imaging devices 14 disposed between the two radiographic imaging devices 14. In this case, when transmitting a transmission signal Fg to a radiographic imaging device 14 that is not directly connected, for example, a signal corresponding to the transmission signal Fg may be sequentially transmitted to the adjacent radiographic imaging devices 14.

The imaging operations of the radiographic imaging devices 14 of the present embodiment may be different from the imaging operations (see FIG. 11) of the radiographic imaging devices 14 of the first embodiment. While in the imaging operations of the radiographic imaging devices 14 of the first embodiment each of the radiographic imaging devices 14 determines whether or not to continue accumulation of charges, in the following, a case in which only the radiographic imaging device $14_2$ determines whether or not to continue accumulation of charges will be described as the imaging operations of the radiographic imaging devices 14 of the present embodiment.

Figure 23:
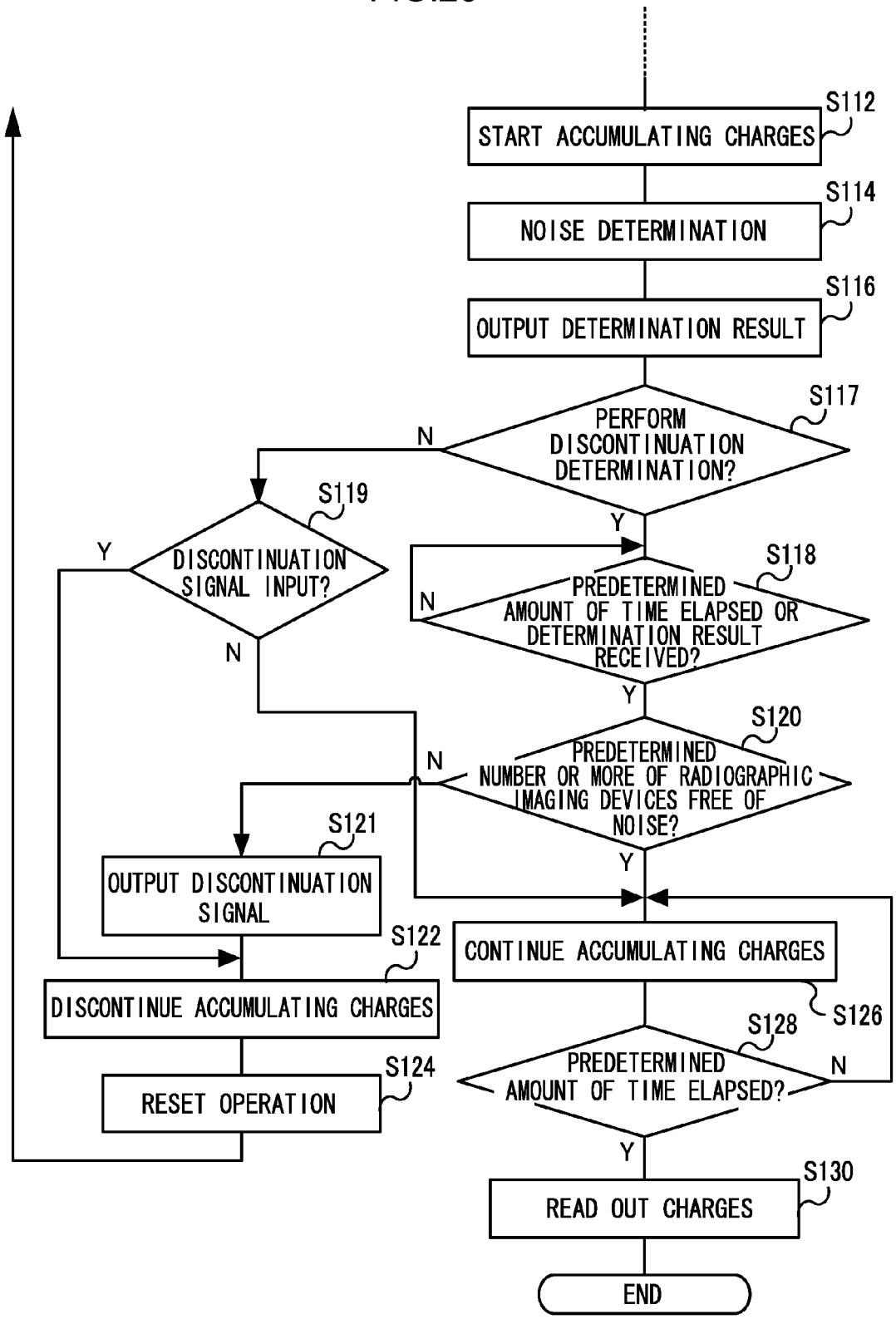
FIG. 23 is a flowchart of an exemplary flow of imaging operations of a radiographic image pertaining to the fourth embodiment.
Figure 24:
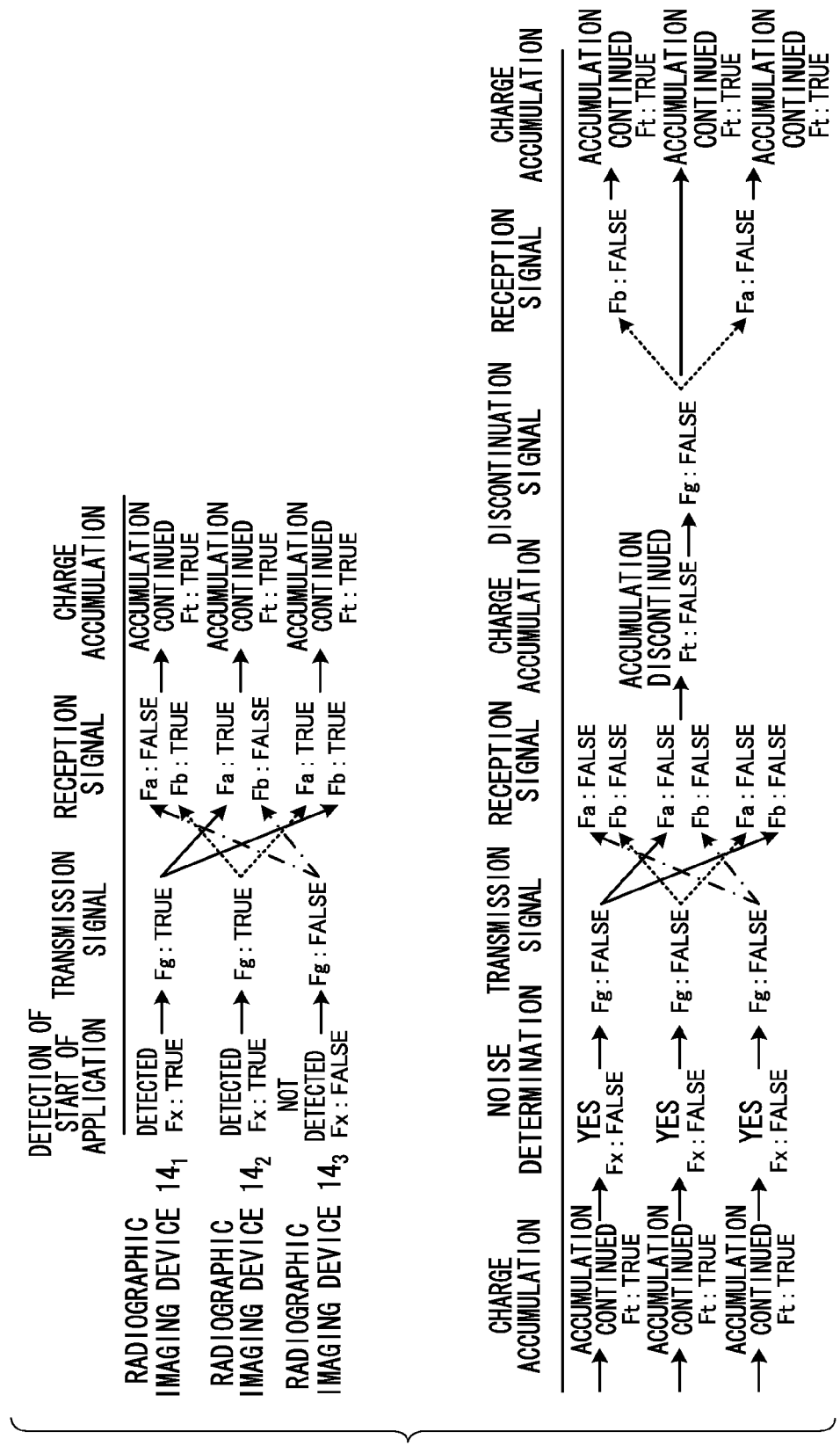
FIG. 24 is an explanatory drawing describing a specific example of signals and flags used in each of the radiographic imaging devices pertaining to the fourth embodiment.

FIG. 23 illustrates a flowchart of an exemplary flow of imaging operations of the radiographic imaging devices 14 of the present embodiment. The processes similar to those in the imaging operations (see FIG. 11) of the radiographic imaging devices 14 of the first embodiment are appended with similar reference numerals and detailed descriptions thereof are omitted Herebelow, a case of a specific example illustrated in FIG. 24 will be described. In the specific example of FIG. 24, the flow until receiving determination result signals are similar to that in the specific example related to the first embodiment illustrated in FIG. 13.

In the imaging operations illustrated in FIG. 23, steps S100 to S116 are similar to those of the imaging operations (see FIG. 11) of the first embodiment.

The imaging operations of the present embodiment proceed to step S117 after step S116. At step S117, the control unit 106 determines whether or not to continue accumulation of charges. Here, information related to whether or not to continue accumulation of charges is stored in advance in a HDD or the like of the control unit 106, and the control unit 106 determines whether or not a determination to continue accumulation of charges should be performed at the local device itself based on this information. As described above, since the radiographic imaging device 14$_2$ determines whether or not to continue accumulation of charges by itself, the determination is affirmative at the radiographic imaging device 14$_2$ and the processing proceeds to step S118.

In steps S118 and S120, whether or not noise has been occurred is determined as in the first embodiment, and if the determination at step S120 is affirmative, the processing proceeds to step S126 where accumulation of charges is continued. Steps S126 to S130 are similar to those of the first embodiment.

In a case in which the determination at step S120 is negative, the processing proceeds to step S121. In step S121, the control unit 106 transmits a discontinuation signal respectively to the radiographic imaging devices 14$_1$ and 14$_3$ and then proceeds to step S122. Here, a low level (FALSE) transmission signal Fg is transmitted to the radiographic imaging devices 14$_1$ and 14$_3$ as the discontinuation signal.

Steps S122 and S124 are similar to those of the first embodiment.

In this way, similarly to the first embodiment, the radiographic imaging device 14$_2$ determines whether or not to continue accumulation of charges and when discontinuing accumulation, transmits a discontinuation signal to the radiographic imaging devices 14$_1$ and 14$_3$.

At the radiographic imaging devices 14$_1$ and 14$_3$, respectively, the determination of step S114 is negative and the processing proceeds to step S119. In step S119, the control unit 106 determines whether or not a discontinuation signal has been input. In a case in which a discontinuation signal has not been input, the determination is negative and the processing proceeds to step S126.

In a case in which a discontinuation signal has been input, the determination of step S119 is affirmative and the processing proceeds to step S122. In the radiographic imaging devices 14$_1$ and 14$_3$, respectively, in a case in which a discontinuation signal (FALSE) has been received after transmission of a determination result, accumulation of charges at the pixels 100 of the radiation detector 26 is discontinued based on the received discontinuation signal. It is preferable that the processing proceeds to step S122 in a case in which a discontinuation signal is received within a predetermined amount of time at step S119.

In this way, the radiographic imaging devices 14$_1$ and 14$_3$ discontinue accumulation of charges based on the discontinuation signal received from the radiographic imaging device 14$_2$.

As described in the above embodiments, the electronic cassette 12 of the radiographic imaging system 10 includes the plural (three) radiographic imaging devices 14 (14$_1$ to 14$_3$). The communication units 30 of the radiographic imaging devices 14$_1$ to 14$_3$ are connected to one another by the signal wires 36. In the first embodiment and the second embodiment, the radiographic imaging devices 14 are connected in parallel to one another. In the third embodiment, the radiographic imaging devices 14 are connected in series to one another.

The control unit 106 of each of the radiographic imaging devices 14 detects the start of the application of the radiation and transmits a detection result signal from the transmission unit 32 to all of the other radiographic imaging devices 14 that are connected. After detecting the start of the application of the radiation, the control unit 106 determines whether or not noise is occurring and transmits a determination result signal from the transmission unit 32 to all of the other radiographic imaging devices 14 that are connected.

In particular, in the radiographic imaging devices 14 of the above embodiments, the detection result signal and the determination result signal are binary (1-bit) signals and are communicated by the signal wires 36 that are hard wires. Thus, the necessary information can be communicated at a high speed.

The control unit 106 of each of the radiographic imaging devices 14 starts accumulating the charges in the pixels 100 in a case in which one or more of the radiographic imaging devices 14 have detected the start of the application of the radiation, based on the detection results of all of the radiographic imaging devices 14. Furthermore, the control unit 106 of each of the radiographic imaging devices 14 continues accumulating the charges in the pixels 100 in a case in which one or more of the radiographic imaging devices 14 have determined that noise is not occurring, based on the determination results of all of the radiographic imaging devices 14.

Each of the radiographic imaging devices 14 may share the detection results and the determination results of all of the radiographic imaging devices 14 included in the electronic cassette 12. Each of the radiographic imaging devices 14 may start and continue accumulating the charges based on the detection results and the determination results of all of the radiographic imaging devices 14. Therefore, operations may be carried out at a high speed and delays in operations can be suppressed compared to a case in which a control unit is separately disposed outside the radiographic imaging devices 14, all of the radiographic imaging devices 14 transmit the detection results and the determination results to the control unit, and the control unit controls the accumulation of the charges in each of the radiographic imaging devices 14 based on the detection results and the determination results.

Consequently, the trackability of incident radiation X is improved, radiation loss is reduced and the percentage of the amount of radiation that does not contribute to the radiographic image decreases, thereby preventing the occurrence of artifacts in the radiographic image.

Furthermore, in a case in which the start of the application of the radiation is a misdetection, the period in which the radiographic imaging devices 14 become insensitive to the radiation until they return again to the radiation application start detection standby state may be shortened.

Furthermore, in the first embodiment and the second embodiment, since the radiographic imaging devices 14 are connected in parallel to one another, the detection result signals and the determination result signals may be communicated at a higher speed.

In the third embodiment, since the number of reception terminals 35 can be reduced to one regardless of the number of radiographic imaging devices 14, the configuration of the radiographic imaging devices 14 may be simplified.

In the above embodiments, the control unit 106 has the function of a detection unit that detects the start of the application of the radiation and the function of a determination unit that determines whether or not noise is occurring. However, it suffices for each of the radiographic imaging devices 14 to have the functions of a detection unit and a determination unit, and the configuration or implementation method are not particularly limited. For example, the control unit 106 may have either one function, and the other function may be implemented by another functional unit (a sensor, a circuit, or a microcomputer). Or, for example, both functions of the detection unit and the determination unit may be realized by another functional unit. The same functional unit may have the functions of the detection unit and the determination unit, or separate functional units may have the functions of the detection unit and the determination unit.

The method of detecting the start of the application and the method of determining whether or not noise is occurring are not limited to the above embodiments. Examples of other methods include methods (1) to (7) described below.

(1) Pixels arbitrarily selected from the radiographic imaging pixels (two-dimensional array) are used as dedicated pixels for radiation detection. In this case, the radiographic imaging pixels and the radiation detection pixels have the same configuration.

(2) Pixels arbitrarily selected from the radiographic imaging pixels (two-dimensional array) are given a configuration in which they are also capable of detecting start of radiation application. That is, some of the pixels are used as pixels for both radiographic imaging and radiation detection. One method for implementing this may be, for example, to divide the sensor portions of the selected pixels into two and use the sensor portions selectively in the case of radiographic imaging and the case of radiation detection. Or, for example, additional TFT switches may be provided in the selected pixels and the start of radiation application may be detected on the basis of leak current in the additionally disposed TFT switches.

(3) Dedicated sensors for radiation detection are arbitrarily disposed between (e.g., in interstices between) the radiographic imaging pixels (two-dimensional array).

In methods (2) and (3), with respect to the configuration of the radiation detector used in these methods, only the selected pixels (the selected interstices) may have this kind of configuration, or the sensor portions and the TFT switches may be repeatedly patterned (i.e., having the same configuration) and the connection thereof may be configured to retrieve the charges only from the selected pixels.

(4) A detection unit is separately disposed without changing the configuration of the radiographic imaging pixels (two-dimensional array) and the interstices between them. Examples of detection methods include detecting the bias current, detecting the gate current, and detecting the leak current of the radiation detector.

(5) A radiographic imaging control unit may also be used without separately disposing a detection unit and without changing the configuration of the radiographic imaging pixels (two-dimensional array) and the interstices between them. Examples of detection methods include detecting the leak current.

Methods (1) to (5) all correspond to a case in which sensors that generate charges (electrical signals) in response to an amount of applied radiation are disposed inside the radiation detector. The methods are not limited to these, and a sensor may be disposed outside the radiation detector as in methods (6) and (7) described below.

(6) A radiation detection sensor is disposed outside the radiation detector. For example, a radiation detection sensor may be disposed at the bottom surface of the radiation detector to which the radiation is not applied.

(7) A vibration sensor is disposed outside the radiation detector. The vibration sensor cannot detect the start of the application of the radiation but may be used to determine whether or not noise is occurring.

In any of the methods (1) to (7), the radiation may be detected in a case in which the gates of the TFT switches are on, or the radiation may be detected in a case in which the gates are off.

The method of communicating the detection result signals and the determination result signals is not limited to the above embodiments provided that both signals are binary (1-bit) signals and can be communicated at a high speed. For example, optical fibers may be used as the signal wires 36. Or, for example, a photocoupler in which a transmission end is a light source such as a light emitting diode (LED) and a reception end is a sensor such as a phototransistor may be provided, and communication may be performed by switching on and off the light source. The signals may also be transmitted as radio waves. Alternatively, a digital circuit may be configured, unique communication protocol in which unnecessary communication headers are deleted from Ethernet (registered trademark) or Bluetooth (registered trademark) may be created, and wire or wireless communication may be performed using these configurations.

In the above embodiments, the determination of whether or not noise is occurring is performed only once. However, embodiments are not limited thereto, and the determination of whether or not noise is occurring may be repeatedly performed. For example, even during the charge accumulation period, the determination of whether or not noise is occurring may be continued in the same way as described above, with all of the radiographic imaging devices 14 sharing the determination results. By continuing the determination, imaging may be quickly cancelled and restart of imaging may be quickly performed in a case in which noise has occurred during imaging (during the accumulation period).

In a case in which the radiographic imaging devices 14 are connected in series to one another as in the third embodiment, the control unit 106 may decide to continue accumulating the charges on the basis of the determination results of the radiographic imaging devices 14 that have detected the start of the application of the radiation as in the second embodiment. Or, in a case in which the radiographic imaging devices 14 are connected in series to one another as in the third embodiment, rather than performing circular referencing as described above, the control unit 106 may store the received detection result signals and determination result signals, and after receiving all of the detection result signals and determination result signals, determine whether or not to start and continue accumulating the charges based on the stored signals.

In the above embodiments, a case has been described in which, as illustrated in FIG. 1, the plural radiographic imaging devices 14 are arranged adjacent to one another in one direction parallel to the subject 18, but the arranged positions and arranging method are not particularly limited thereto. For example, four radiographic imaging devices 14 may be arranged in a manner in which two in one direction parallel to the subject 18 and two in a direction intersecting the one direction (2×2=4 radiographic imaging devices).

Figure 25:
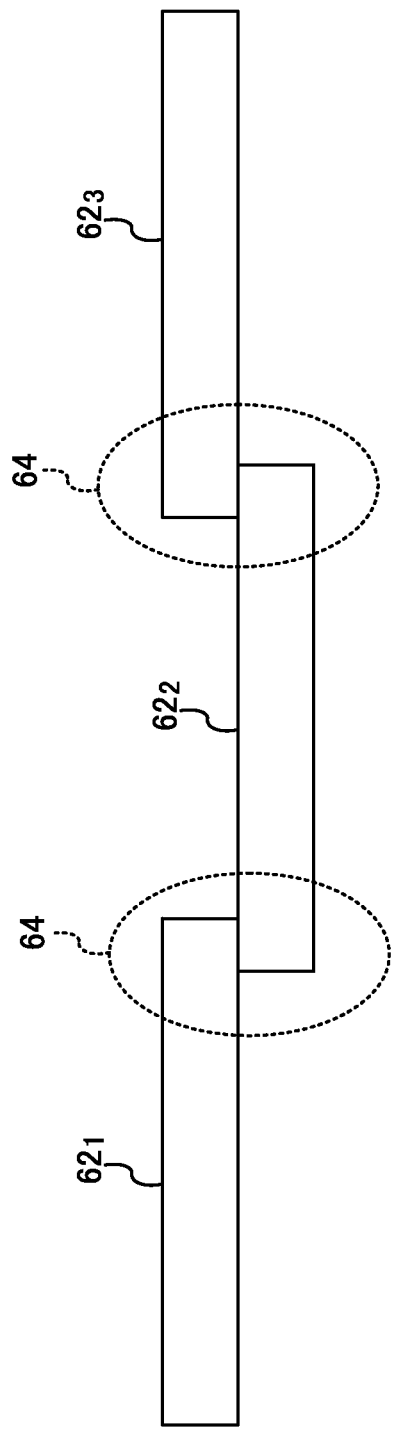
FIG. 25 is a schematic configuration diagram for describing an example in which plural electronic cassettes are disposed adjacent to one another.
Figure 26:
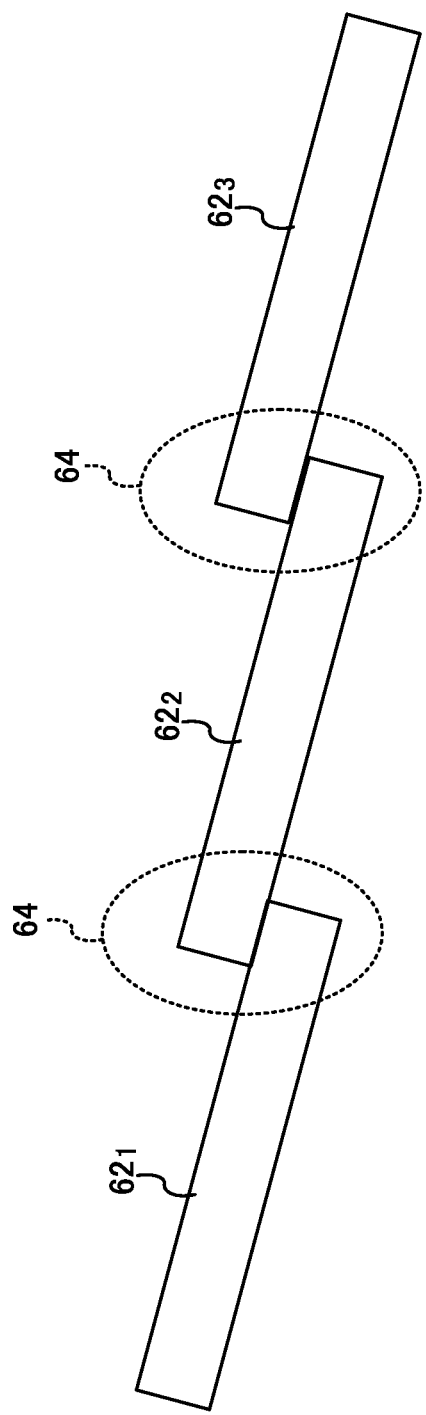
FIG. 26 is a schematic configuration diagram for describing another example in which plural electronic cassettes are disposed adjacent to one another.

In the above embodiments, a case has been described in which the plural radiographic imaging devices 14 are disposed in the casing 13 of the one electronic cassette 12, but the present disclosure may also be applied to a radiographic imaging system including plural electronic cassettes. For example, a configuration may be made in which a long imaging plane is provided by arranging plural electronic cassettes, each having one radiographic imaging device, adjacent to one another. Specific example configurations of cases in which plural electronic cassettes are arranged adjacent to one another are illustrated in FIG. 25 and FIG. 26. FIG. 25 and FIG. 26 illustrates cases in which three electronic cassettes 62 (62₁ to 62₃) are arranged adjacent to one another.

In both of the cases illustrated in FIG. 25 and FIG. 26, the signal wires (which correspond to the signal wires 36 of the above embodiments), transmission terminals, and reception terminals connecting each of the electronic cassettes 62 are preferably disposed inside the electronic cassettes 62, and the electronic cassettes 62 are preferably connected to one another via connection portions 64. For example, signal wires for interconnecting the electronic cassettes 62 may be disposed in inner walls of the electronic cassettes 62, and the signal wires may be connected to the transmission terminals and reception terminals.

The above embodiments have been described as cases in which the present disclosure is applied to the indirect conversion type radiation detector 26 that converts the radiation into light and then converts the light into charges. However, embodiments are not limited to this and, for example, the present disclosure may be applied to a direct conversion type radiation detector that uses, as a photoelectric conversion layer that absorbs and converts radiation into charges, a material such as amorphous selenium that directly converts radiation.

In addition, the configurations and operations of the radiographic imaging system 10, the electronic cassette 12, and the radiographic imaging devices 14 described in the embodiments are examples and, obviously, may be modified depending on the situation without departing from the spirit of the present disclosure.

Furthermore, in the embodiments, the radiation is not particularly limited, and X-rays or gamma rays may be applied.

What is claimed is:

1. A radiographic imaging system including:
   a plurality of radiographic imaging devices that image a same subject with same applied radiation, each of the plurality radiographic imaging devices comprising:
      a radiation detector including a plurality of pixels, each of the plurality of pixels including a sensor portion that generates a charge corresponding to an amount of applied radiation and accumulates the generated charge, and a switch element for reading out the charge from the sensor portion;
      a sensor configured to generate electrical signals in accordance with application of radiation on the radiation detector;
      a detection unit configured to detect whether or not application of the radiation has been started with respect to the radiation detector, based on the electrical signals generated by the sensor;
      a determination unit configured to determine whether or not noise is superimposed on the electrical signals after the detection unit has detected whether or not the application of the radiation has been started with respect to the radiation detector; and
      a communication unit that is connected to another radiographic imaging device and transmits to and receives from the other connected radiographic imaging device a detection result signal indicating detection results of the detection unit and a determination result signal indicating a determination result of the determination unit.

2. The radiographic imaging system according to claim 1, wherein the detection result signal and the determination result signal are binary signals.

3. The radiographic imaging system according to claim 1, wherein each of the plurality of radiographic imaging devices further comprises a control unit configured to effect control of starting accumulation of the charges generated by the sensor portions in a case in which it is determined, based on the detection result signal received via the communication unit, that the detection unit included in at least a first predetermined number of the plurality of radiographic imaging devices has detected the start of the application of the radiation, the first predetermined number being a positive integer.

4. The radiographic imaging system according to claim 3, wherein the control unit is further configured to effect control of continuing accumulation of the charges generated by the sensor portions in at least one case of:
   (a) a case in which the determination unit included in at least a second predetermined number of the plurality of radiographic imaging devices has determined that noise is not superimposed on the electrical signals, the second predetermined number being a positive integer, or
   (b) a case in which the determination unit included in at least a third number of the plurality of radiographic imaging devices, in which the start of the application of the radiation has been detected by the detection unit, has determined that noise is not superimposed on the electrical signals, the third predetermined number being a positive integer.

5. The radiographic imaging system according to claim 3, wherein the control unit is further configured to effect control of discontinuing accumulation of the charges generated by the sensor portions in at least one case of:
   (c) a case in which the determination units included in all of the plurality of radiographic imaging devices, connected to the communication unit, have determined that noise is superimposed on the electrical signals, or
   (d) a case in which the determination units included in all of the radiographic imaging devices, in which the start of the application of the radiation has been detected by the detection units, have determined that noise is superimposed on the electrical signals.

6. The radiographic imaging system according to claim 5, wherein
   the control unit is further configured to release the charges accumulated in the sensor portions after discontinuing accumulation of the charges generated by the sensor portions, and
   the detection unit is further configured to detect whether or not the application of the radiation has been started again with respect to the radiation detector.

7. The radiographic imaging system according to claim 1, further comprising a single casing that houses the plurality of radiographic imaging devices.

8. The radiographic imaging system according to claim 7, wherein the single casing also houses the sensor that is configured to generate electrical signals in accordance with application of radiation on the radiation detector.

9. The radiographic imaging system according to claim 1, wherein the detection unit is further configured to detect whether or not the application of the radiation has been started based on whether or not the electrical signals satisfy a preset condition.

10. A radiographic imaging device comprising:
    a radiation detector including a plurality of pixels, each of the plurality of pixels including a sensor portion that generates a charge corresponding to an amount of applied radiation and accumulates the generated charge, and a switch element for reading out the charge from the sensor portion;

a sensor configured to generate electrical signals in accordance with application of radiation on the radiation detector;

a detection unit configured to detect whether or not application of the radiation has been started with respect to the radiation detector based on the electrical signals generated by the sensor;

a determination unit configured to determine whether or not noise is superimposed on the electrical signals after the detection unit has detected whether or not the application of the radiation has been started with respect to the radiation detector; and a communication unit that is connected to another radiographic imaging device, which images a same subject with same applied radiation, and transmits to and receives from the other connected radiographic imaging device a detection result signal indicating detection results of the detection unit and a determination result signal indicating a determination result of the determination unit.

11. A method of controlling radiographic imaging devices in a radiographic imaging system including a plurality of radiographic imaging devices that image a same subject with same applied radiation and are connected to one another via communication units, each of the plurality of radiographic imaging devices including a radiation detector in which a plurality of pixels are disposed, each of the plurality of pixels including a sensor portion that generates a charge corresponding to an amount of the applied radiation and accumulates the generated charge, and a switch element for reading out the charge from the sensor portion, and each of the plurality of radiographic imaging devices including a sensor configured to generate electrical signals in accordance with application of radiation on the radiation detector, the method comprising:

detecting whether or not the application of the radiation has been started with respect to the radiation detector based on the electrical signals generated by the sensor;

determining whether or not noise is superimposed on the electrical signals after detecting whether or not the application of the radiation has been started with respect to the radiation detector; and transmitting to and receiving from another connected radiographic imaging device a detection result signal indicating detection results and a determination result signal indicating a determination result.

12. The radiographic imaging device control method according to claim 11, wherein the detection result signal and the determination result signal are binary signals.

13. A non-transitory storage medium storing a program that causes a computer to execute processing for controlling each of radiographic imaging devices in a radiographic imaging system in which a plurality of radiographic imaging devices are connected to one another, each of the radiographic imaging devices including a radiation detector and a sensor configured to generate electrical signals in accordance with application of radiation on the radiation detector, the processing comprising:

detecting whether or not application of radiation has been started with respect to the radiation detector on the basis of the electrical signals generated by the sensor;

determining whether or not noise is superimposed on the electrical signals after detecting whether or not the application of the radiation has been started with respect to the radiation detector; and transmitting to and receiving from another connected radiographic imaging device a detection result signal indicating the detection results and a determination result signal indicating a determination result.

* * * * *